(12) United States Patent
Rusch et al.

(10) Patent No.: US 12,090,305 B2
(45) Date of Patent: *Sep. 17, 2024

(54) MEDICAL DELIVERY DEVICE WITH LAMINATED STOPPER

(71) Applicant: W. L. Gore & Associates, Inc., Newark, DE (US)

(72) Inventors: Greg Rusch, Newark, DE (US); Robert C. Basham, Forest Hill, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 302 days.

This patent is subject to a terminal disclaimer.

(21) Appl. No.: 17/661,907

(22) Filed: May 3, 2022

(65) Prior Publication Data

US 2022/0257866 A1  Aug. 18, 2022

Related U.S. Application Data

(63) Continuation of application No. 16/591,844, filed on Oct. 3, 2019, now Pat. No. 11,439,757, which is a
(Continued)

(51) Int. Cl.
*A61M 5/315* (2006.01)
*A61L 31/04* (2006.01)
*A61M 5/31* (2006.01)

(52) U.S. Cl.
CPC ....... *A61M 5/31505* (2013.01); *A61L 31/048* (2013.01); *A61M 5/31513* (2013.01);
(Continued)

(58) Field of Classification Search
CPC .......... A61M 5/31505; A61M 5/31513; A61M 2005/3101; A61M 2005/31506;
(Continued)

(56) References Cited

U.S. PATENT DOCUMENTS

| 4,303,070 A | 12/1981 | Ichikawa et al. |
| 5,009,646 A | 4/1991 | Daikyo |

(Continued)

FOREIGN PATENT DOCUMENTS

| EP | 0026940 | 5/1984 |
| EP | 2796159 A1 | 10/2014 |

(Continued)

OTHER PUBLICATIONS

International Standard ISO 11040-5, Prefilled syringes Part 5: Plunger stoppers for injectables, 2012, 10 pages.
(Continued)

*Primary Examiner* — Lauren P Farrar
(74) *Attorney, Agent, or Firm* — W. L. Gore & Associates, Inc.; Amy L. Miller

(57) ABSTRACT

The present disclosure relates to a medical delivery device that includes a barrel having an inner surface, a plunger rod having a distal end inserted within the barrel, and a stopper attached to the distal end of the plunger rod and contacting at least a portion of the inner surface of the barrel. In at least one embodiment, the inner surface is hydrophilic. The stopper may include an elastomeric body, one or more fluoropolymer layers, and two or more ribs laminated with the one or more fluoropolymer layers. In some embodiments, the contact width between at least one rib having a sealing surface and the portion of the inner surface of the barrel measured at a compressibility of greater than about 7.9% of the stopper is less than about 1.0 mm.

17 Claims, 6 Drawing Sheets

Related U.S. Application Data continuation of application No. 15/404,892, filed on Jan. 12, 2017, now Pat. No. 10,471,211.

(60) Provisional application No. 62/279,553, filed on Jan. 15, 2016.

(52) U.S. Cl.
CPC ............ *A61M 2005/3101* (2013.01); *A61M 2005/31506* (2013.01); *A61M 2205/0216* (2013.01); *A61M 2205/0222* (2013.01); *A61M 2205/0238* (2013.01)

(58) Field of Classification Search
CPC ............ A61M 2205/0216; A61M 2205/0222; A61M 2205/0238; A61L 31/048
See application file for complete search history.

(56) References Cited

U.S. PATENT DOCUMENTS

| | | | |
|---|---|---|---|
| 5,374,473 A | 12/1994 | Knox et al. | |
| 5,708,044 A | 1/1998 | Branca | |
| 5,792,525 A | 8/1998 | Fuhr et al. | |
| 6,030,694 A | 2/2000 | Dolan et al. | |
| 6,541,589 B1 | 4/2003 | Baillie | |
| 7,521,010 B2 | 4/2009 | Kennedy | |
| 7,531,611 B2 | 5/2009 | Sabol | |
| 8,637,144 B2 | 1/2014 | Ford | |
| 8,658,707 B2 | 2/2014 | Xu et al. | |
| 8,722,178 B2 | 5/2014 | Ashmead et al. | |
| 8,960,685 B2 | 2/2015 | Maeda et al. | |
| 9,139,669 B2 | 9/2015 | Xu et al. | |
| 2011/0137263 A1 | 6/2011 | Ashmead et al. | |
| 2012/0251748 A1 | 10/2012 | Ashmead et al. | |
| 2012/0260607 A1 | 10/2012 | Moritz | |
| 2015/0148751 A1* | 5/2015 | Yotsutsuji ......... | A61M 5/31513 604/218 |
| 2016/0015898 A1 | 1/2016 | Jones et al. | |
| 2016/0022918 A1 | 1/2016 | Gunzel | |

FOREIGN PATENT DOCUMENTS

| | | |
|---|---|---|
| EP | 2803378 | 11/2014 |
| JP | A-1982022766 | 2/1982 |
| JP | 10024105 A | 1/1989 |
| JP | A-1998024105 | 1/1998 |
| JP | 2006-519070 | 8/2006 |
| JP | 2013509270 | 3/2013 |
| JP | A-2014213092 | 11/2014 |
| JP | A-2014223149 | 12/2014 |
| WO | WO-2011059823 A1 | 5/2011 |
| WO | WO-2014/196057 | 12/2014 |
| WO | WO-2015/016170 | 2/2015 |

OTHER PUBLICATIONS

Krayukhina, et al. "Effects of Syringe Material and Silicone Oil Lubrication on the Stability of Pharmaceutical Proteins," Journal of Pharmaceutical Sciences, vol. 104, pp. 527-535, 2015.

* cited by examiner

MEDICAL DELIVERY DEVICE WITH LAMINATED STOPPER

FIELD

The present invention relates to a medical delivery device with a laminated stopper, and in particular, to a medical delivery device with a stopper laminated with a fluoropolymer film.

BACKGROUND

Medical delivery devices such as syringes typically include a barrel, a plunger rod reciprocally movable in the barrel, and a stopper attached to an end of the plunger rod. The stopper to be used for the syringe is typically air and liquid impermeable while also possessing low-friction slidability. Air and liquid impermeability is important for eliminating liquid leakage within the barrel and the introduction of air between an outer face of the stopper and an inner wall of the barrel when charging or discharging the liquid inside the syringe. Low-friction slidability is important for facilitating the charging and discharging of the liquid inside the syringe. In addition to these requirements, a medical syringe, in particular, must not adversely affect any pharmaceutical composition such as biopharmaceuticals that come in contact with the syringe (e.g., a pre-filled syringe comprising a pharmaceutical composition).

Stoppers for conventional syringes are commonly made of a rubber material such as natural rubber, isoprene rubber or styrene-butadiene rubber which may be vulcanized. Although this type of conventional stopper has satisfactory air and liquid impermeability, it does not have good low-friction slidability. Accordingly, silicone lubricants are typically applied to both the outer face of the stopper and the inner wall of the barrel such that the stopper can slide within the barrel. However, syringes comprising silicone lubricants cannot be used for pharmaceutical composition and the like because the silicone lubricant can cause inactivation or otherwise impact the efficacy of these pharmaceutical compositions. Therefore, in order to maintain the stability of the pharmaceutical composition, stoppers laminated with a fluoropolymer film have been used. Since the air and liquid impermeability of stoppers may also have an impact on the quality and stability of the pharmaceutical compositions, the stoppers laminated with a fluoropolymer film are required to have high levels of air and liquid impermeability. However, when stoppers laminated with a fluoropolymer film are used with a glass or resin syringe having a hydrophilic or lubricant free inner surface, the stoppers undesirably exhibit poorer air and liquid impermeability than conventional, non-laminated rubber stoppers.

Another problem associated with some fluoropolymer laminates is its ability to maintain air and liquid impermeability while also possessing low-friction slidability. For example, some fluoropolymer laminates function inconsistently and can distort during insertion of the plunger rod into the barrel and/or during movement of the plunger rod within the barrel, which can create leak paths for the liquid. Additional difficulties with some fluoropolymer laminates include poor airtightness due to a rough outer surface especially when manufactured as a skived film.

Accordingly, the need exists for stoppers laminated with a fluoropolymer film that are capable of achieving sufficient contact with a hydrophilic or lubricant free inner surface of a barrel of a glass or resin syringe to achieve high levels of air and liquid impermeability while also maintaining acceptably low break loose and slide forces (i.e., low-friction slidability) but not so much contact that the fluoropolymer film is distorted to create leak paths that decrease air and liquid impermeability.

SUMMARY

One embodiment relates to a medical delivery device that includes a barrel, a plunger rod having a distal end inserted within the barrel, a stopper attached to the distal end of the plunger rod and contacting at least a portion of the inner surface of the barrel. The stopper has an elastomeric body, one or more fluoropolymer layers, and two or more ribs laminated with the one or more fluoropolymer layers. A contact width between at least one of the two or more ribs having a sealing surface and a portion of the inner surface of the barrel measured at a compressibility of greater than about 7.9% of the stopper is less than about 1.0 mm. In at least one embodiment, the barrel has a hydrophilic inner surface. Optionally, the hydrophilic inner surface is bare glass (e.g., free or substantially free of silicone oil).

In some embodiments, the medical delivery device further includes a sliding surface that is less than about 2.0 mm, which is calculated based on a sum of the contact widths between at least one of the two or more ribs having a sealing surface and the portion of the inner surface of the barrel measured at a compressibility of greater than about 7.9%.

In some embodiments, at least one of: each rib of the two or more ribs having a sealing surface includes a radius of curvature at an apex of each respective rib that is less than about 0.22 mm; and a ratio of a maximum outer diameter of all the ribs having a sealing surface to an inner diameter of the inner surface of the barrel is nominally greater than about 1.08.

In some embodiments, a maximum outer diameter of the ribs having a sealing surface is greater than about 5.0 mm, an inner diameter of the inner surface of the barrel is nominally between about 4.65 and about 11.85 mm, and a ratio of the maximum outer diameter of the ribs having a sealing surface to an inner diameter of the inner surface of the barrel is greater than about 1.08.

In another embodiment, a plunger rod includes a distal end that is insertable into a barrel and a stopper attached to the distal end. In one or more embodiment, the barrel has a hydrophilic inner surface. The stopper is configured to contact at least a portion of the inner surface of the barrel. The stopper includes an elastomeric body, one or more fluoropolymer layers, and two or more ribs laminated with the one or more fluoropolymer layers. Each rib of the two or more ribs having a sealing surface includes a radius of curvature at an apex of each respective rib that is less than about 0.22 mm, and a ratio of a maximum outer diameter of all the ribs having a sealing surface to an inner diameter of the inner surface of the barrel is greater than about 1.08. The plunger rod may be configured such that when the plunger rod is inserted in the barrel having an inner diameter of an inner surface of the barrel, a contact width between at least one of the two or more ribs having a sealing surface and the portion of the inner surface of the barrel measured at a compressibility of greater than about 7.9% of the stopper is less than about 1.0 mm.

In yet another embodiment, a stopper that is insertable in a barrel having a hydrophilic inner surface comprises an elastomeric body, one or more fluoropolymer layers, and two or more ribs. The at least one of the two or more ribs are laminated with the one or more fluoropolymer layers and configured to contact at least a portion of the inner surface of the barrel. each rib of the two or more ribs having a sealing surface comprises a radius of curvature at an apex of each respective rib that is less than 0.22 mm, and a ratio of a maximum outer diameter of all the ribs having a sealing surface to an inner diameter of the inner surface of the barrel is greater than 1.08, and wherein the stopper is configured such that when the stopper is inserted in the barrel having an inner diameter of an inner surface of the barrel, a contact width between at least one of the two or more ribs having a sealing surface and the portion of the inner surface of the barrel measured at a compressibility of greater than 7.9% of the stopper is less than about 1.0 mm.

Optionally, the one or more fluoropolymer layers described herein may include a single layer of densified expanded polytetrafluoroethylene (ePTFE), or the one or more fluoropolymer layers may include a composite fluoropolymer film having a barrier layer and a porous layer, the barrier layer including densified ePTFE, polytetrafluoroethylene (PTFE), fluorinated ethylene propylene (FEP), polyethylene, polypropylene, polyvinylidene fluoride, polyvinylfluoride, perfluoropropylevinylether, a perfluoroalkoxy polymer, and copolymers and combinations thereof.

BRIEF DESCRIPTION OF THE DRAWINGS

The present invention will be better understood in view of the following non-limiting figures, in which.

DETAILED DESCRIPTION

I. Introduction

Figure 1:
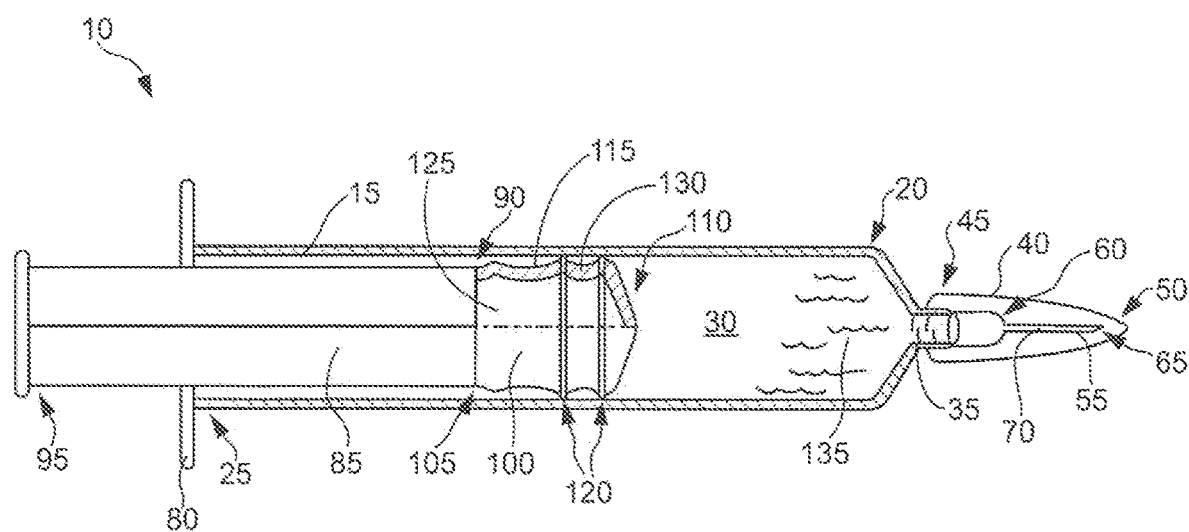
FIG. 1 illustrates a partial cross sectional side view of a syringe in accordance with some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the figures should not be construed as limiting.

The present disclosure is directed to a medical delivery device (e.g., a syringe), a plunger rod and a stopper laminated with a fluoropolymer film. The fluoropolymer laminate provides a low friction barrier between an elastomeric stopper and a pharmaceutical composition (e.g., a drug, medicine or other therapeutic) in the medical delivery device, and may inhibit materials from leaching from the elastomeric stopper or from extraction of compounds from the pharmaceutical composition by the elastomer. Fluoropolymer laminates have good biocompatibility, have good mechanical integrity, are inert, and are processable.

In some embodiments, the stopper has a compressibility (C %) that is greater than about 7.9%, between about 9.5 and about 20.0%, between about 11.75 and about 18.5%, between about 14.0 and about 14.5. In one exemplary embodiment, the compressibility may be about 14.4%. In addition, the stopper includes at least two ribs laminated with a fluoropolymer layer. At least one rib with a sealing surface preferably has a contact width (w) measured at the compressibility (C %) of less than about 1.0 mm. In some embodiments, the contact width at the compressibility is between about 0.05 mm and about 1.0 mm, between about 0.1 and about 0.75 mm, or between about 0.2 and about 0.5 mm.

In some embodiments, the stopper also includes a sliding surface (S), which is a sum of the contact widths (w) of all the ribs having a sealing surface. The sliding surface may be less than about 2.0 mm, or between about 0.05 mm and about 1.9 mm, between about 0.1 mm and about 1.65 mm, or between about 0.5 mm and about 1.25 mm. Optionally, at least one rib having a sealing surface has a predefined radius of curvature (r) at the apex of the rib of less than about 0.22 mm, between about 0.05 and about 0.20 mm, or between about 0.12 and about 0.17 mm. Additionally or alternatively, the ratio of a maximum outer diameter (v) of at least one rib having a sealing surface to an inner diameter (y) of the inner surface of the barrel is greater than about 1.08, between about 1.10 and about 1.25, or between about 1.13 and about 1.23.

In certain embodiments, the fluoropolymer layer may include a fluoropolymer film, such as a polytetrafluoroethylene (PTFE) or densified expanded polytetrafluoroethylene (ePTFE) film. Films based on PTFE or ePTFE can provide thin and strong barrier layers to leachables and extractables. The superior strength of the expanded fluoropolymer structure allows these materials to form thin barriers, which remain intact during the forming process and installation of the stopper into the syringe barrel.

The use of at least partially porous and advantageously fibrilizing materials, such as ePTFE in combination with other materials, provides numerous advantages. In one aspect, the use of such porous materials may provide a scaffold that enables thin strong barrier layers to be made and improves the bond between the elastomer and the laminate. Laminate compliance is beneficial to maintaining a seal between the stopper and the barrel. Porous materials also provide for improved compliance of the stopper. Improved compliance may result from reduced film thickness, flexural compliance, and/or the compressibility of one or more layers of the porous material. Accordingly, by providing a laminate that is at least partially porous to the outside (e.g. external or outermost surface) of the stopper, the seal between the stopper and syringe barrel may be improved while the sliding force is minimized.

The laminate may be of single layer or multiple layer construction. As described herein, layers may be described functionally. However, the functional names of the various layers in the descriptions of embodiments that follow may not describe all of the potential functions of any given layer. Accordingly, it will be understood that such functional nomenclature is not intended to be limiting of any layer property. For example, a laminate layer may have additional properties and functions such as providing a low friction surface, increasing bond strength and the like. Moreover, in multi-layer embodiments, each layer may contribute to the reduction of leachable and extractable materials regardless of its designation as a barrier layer or otherwise.

II. Syringe

FIG. 1 depicts a syringe 10 (optionally a prefilled syringe) in accordance with at least one embodiment. As the skilled artisan will appreciate, although the present invention is described hereafter as it relates to a syringe, other types of medical delivery devices are contemplated, such as, for example, an auto-injector or cartridge, without departing from the spirit and scope of the present disclosure. The syringe 10 includes a barrel 15 having opposed distal and proximal ends 20 and 25 and a receiving chamber 30 positioned between the distal and proximal ends 20 and 25. The barrel 15 may be formed of a substantially rigid or hard material, such as a glass material (e.g., borosilicate glass), a ceramic material, one or more polymeric materials (e.g., polypropylene, polyethylene, and copolymers thereof), a metallic material, or a plastic material (e.g., cyclic olefin polymers (COC) and cyclic olefin copolymers (COP), and combinations thereof.

In certain embodiments, the barrel 15 is formed of glass (e.g., bare glass, without any lubricants thereon), resin, plastic, metal, or like materials and optionally has a hydrophilic interior wall characterized by the absence of a lubricant such as, but not limited to, silicone or silicone oil. As used herein, the term "hydrophilic interior wall" refers to a material (e.g., bare glass that is free or substantially free of silicone oil) that has a contact angle of deionized water on a flat surface of the material of less than about 90°, which indicates high wettability.

The distal end 20 of barrel 15 includes an elongated tip 35 extending through and communicating with the receiving chamber 30. In some embodiments, a cap 40 is disposed at the distal end 20 of the barrel 15. The cap 40 includes a proximal end 45 mated to the distal end 20 or to the elongated tip 35 and a closed distal end 50. Thus, the cap 40 inhibits or prevents ambient air from communicating with the receiving chamber 30 through the elongated tip 35. Optionally, a piercing element 55 is also disposed at the distal end 20 of the barrel 15. The piercing element 55 includes a proximal end 60 mated to the distal end 20 or to the elongated tip 35 and a distal end 65. It is within the purview of the present disclosure that the piercing element 55 may include a sharply pointed needle cannulae, or a blunt-ended cannulae, such as those employed with "needleless" systems. For purposes of illustration, the piercing element 55 depicted and described herein is formed as a sharply pointed, elongate needle cannula 55 including the proximal end 60, a sharply pointed distal end 65 and a lumen 70 extending between the proximal end 60 and the distal end 65. Proximal end 60 of needle cannula 55 may be rigidly mounted to the elongated tip 35 of the barrel 15.

In some embodiments, the cap 40 is mounted over needle cannula 55 and is releasably engaged to the elongated tip 35 of the barrel 15. The cap 40 may be formed from a rigid material such as plastic, or can be formed from a flexible material such as rubber, or from like materials or combinations known to the skilled artisan. The cap 40 may be configured for closing the lumen 70 of the needle cannula 55 in fluid communication with a pharmaceutical composition, and/or to otherwise protectively seal, engage or surround sharply pointed distal end 65 of needle cannula 55 and isolate same from the ambient environment. Thus, the cap 40 prevents ambient air from communicating with the receiving chamber 30 through needle cannula 55.

The proximal end 25 of barrel 15 may include a flange 80 to be used as a finger stopper for pressing and pulling a plunger rod 85 reciprocally in the barrel 15. The plunger rod 85 has opposed distal and proximal ends 90 and 95 with a stopper 100 attached to the distal end 90. Stopper 100 includes opposed proximal and distal ends 105 and 110 and a side surface 115 extending therebetween. The side surface 115 of stopper 100 may include two or more ribs 120 such as one or more circumferentially extending annular ribs. The stopper 100 is preferably formed of an elastomeric body 125 and one or more laminate layers 130. The elastomeric body 125 may include any suitable elastomer, and more particularly, rubbers constructed from butyl, bromobutyl, chlorobutyl, silicone, nitrile, styrene butadiene, polychloroprene, ethylene propylene diene, fluoroelastomers, thermoplastic elastomers (TPE), and combinations and blends thereof. In some embodiments, the elastomeric body 125 may have an initial modulus (small strain) of between about 2.5 MPa to about 5 MPa, or between about 3 MPa to about 4 MPa. In one non-limiting embodiment, the initial modulus may be, for example, about 3.5 MPa (plus/minus measurement and variability tolerance). The materials of the one or more laminate layers 130 are chosen, as described in detail herein, to provide a low coefficient of friction, compliance, low extractables and leachables, and good barrier properties as they relate to extractables and leachables from the elastomeric body 125, as well as good air and liquid impermeability. For example, the one or more laminate layers 130 may include one or more fluoropolymer films, such as, but not limited to PTFE or ePTFE films.

FIG. 1 also shows a material 135 provided in the receiving chamber 30 of barrel 15 (e.g., a prefilled syringe). For purposes of illustration but not of limitation, the material 135 is herein identified as a predetermined dose of a pharmaceutical composition 135; however, it should be understood that the material 135 could be any type of liquid or material capable of being expelled from a syringe, or the material 135 may be all together absent from the receiving chamber (e.g., an unfilled syringe).

III. Laminate Layers

Figure 2:
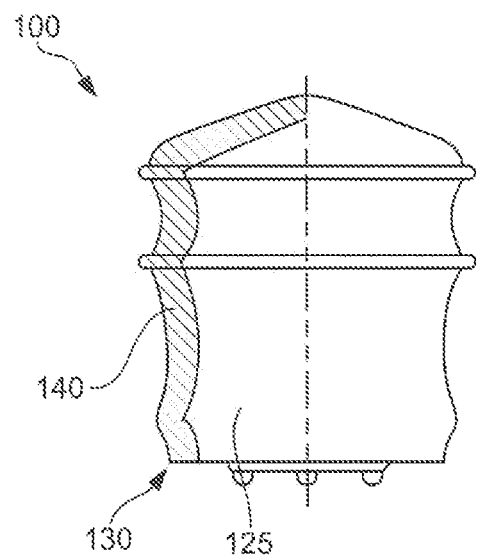
FIGS. 2-9 depict cross sectional side views of stoppers in accordance with some embodiments.

In some embodiments, the one or more laminate layers 130 may include a single layer of a fluoropolymer. FIG. 2 depicts a stopper 100 that includes an elastomeric body 125 and a single layer of fluoropolymer or barrier layer 140. Examples of elastomers that can be used to form the elastomeric body 125 include any elastomer suitable for the application, most notably rubbers constructed from butyl, bromobutyl, chlorobutyl, silicone, nitrile, styrene butadiene, polychloroprene, ethylene propylene diene, fluoroelastomers, thermoplastic elastomers (TPE), thermoplastic vulcanizates (TPV), and materials sold under the trade name VITON®, and combinations and blends thereof. Exemplary elastomeric materials include, but are not limited to, butyl rubber, bromobutyl rubber, chlorobutyl rubber, silicone, nitrile, styrene butadiene, polychloroprene, ethylene propylene diene, fluoroelastomers and combinations thereof.

Examples of fluoropolymers that can be used to form the fluoropolymer or barrier layer 140 include any fluoropolymer suitable for the application, most notably a densified expanded fluoropolymer, polytetrafluoroethylene (PTFE), densified ePTFE, fluorinated propylene (FEP), polyethylene, polypropylene, polyvinylidene fluoride, polyvinylfluoride, perfluoropropylevinylether, perfluoroalkoxy polymers, tetrafluoroethylene (TFE), and copolymers and combinations thereof. The barrier film may also include a composite fluoropolymer film having a barrier layer and a porous layer. The porous layer, for example, maybe formed of ePTFE or other porous expanded and fibrilizing fluoropolymers (for example, ePTFE as taught in U.S. Pat. No. 6,541,589). The ePTFE layers may be filled with an organic or inorganic material to provide color, lubricity, or other function.

In a some embodiments, the fluoropolymer or barrier layer 140 may include a densified expanded fluoropolymer, preferably a densified expanded polytetrafluoroethylene (ePTFE). A densified ePTFE film may be prepared in the manner described in U.S. Pat. No. 7,521,010 to Kennedy, et al., U.S. Pat. No. 6,030,694 to Dolan et al., U.S. Pat. No. 5,792,525 to Fuhr et al., or U.S. Pat. No. 5,374,473 to Knox et al. Expanded copolymers of PTFE, such as are described in U.S. Pat. No. 5,708,044 to Branca, U.S. Pat. No. 6,541,589 to Baillie, U.S. Pat. No. 7,531,611 to Sabol et al., U.S. Pat. No. 8,637,144 to Ford, and U.S. Pat. No. 9,139,669 to Xu et al. may be utilized if they are densified.

The barrier film may also include an expanded polymeric material including a functional tetrafluoroethylene (TFE) copolymer material having a microstructure characterized by nodes interconnected by fibrils, where the functional TFE copolymer material includes a functional copolymer of TFE and PSVE (perfluorosulfonyl vinyl ether), or TFE with another suitable functional monomer, such as, but not limited to, vinylidene fluoride (VDF), vinyl acetate, or vinyl alcohol. The functional TFE copolymer material may be prepared, for example, according to the methods described in U.S. Pat. No. 9,139,669 to Xu et al. or U.S. Pat. No. 8,658,707 to Xu et al.

The densified ePTFE film may be combined with an elastomer to construct the stopper 100. In this embodiment, the densified ePTFE film is thermoformed to make a preform. Thermoforming is done at process temperatures sufficiently above the nodal melt temperature to ensure melt forming while preserving barrier and strength properties. The high strength of the resulting expanded film allows for forming extremely thin films. The films can be made with thicknesses ranging from about 0.5 micron to about 20 microns. In some embodiments, the films have a thickness that is less than about 30 microns. The film can optionally be pre-treated or post-treated with chemical etching, plasma treating, corona, roughening, or the like to improve bonding to the elastomeric body 125. The thermoformed, densified ePTFE preform can be combined with the elastomeric body 125 by injection molding, compression molding, priming and post laminating around an elastomer perform, or by other suitable methods known to those of skill in the art.

Figure 3:
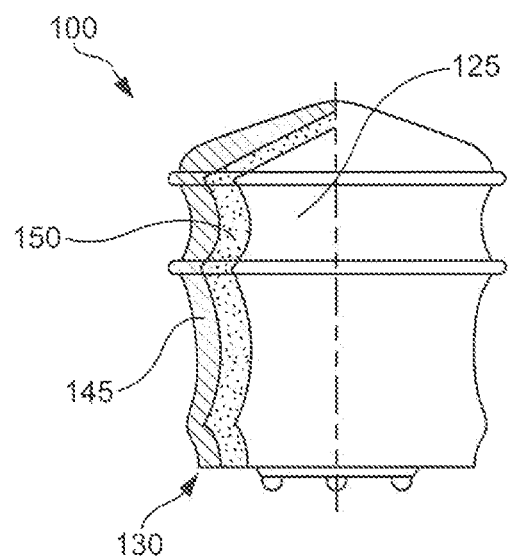

In another embodiment, as shown in FIG. 3, the one or more laminate layers 130 may include a composite fluoropolymer film having a barrier layer 145 and a porous layer 150. The barrier layer 145 can include a fluoropolymer such as a densified expanded fluoropolymer, PTFE, ePTFE, densified ePTFE, FEP, polyethylene, polypropylene, polyvinylidene fluoride, polyvinylfluoride, perfluoropropylevinylether, perfluoroalkoxy polymers, TFE, and copolymers and combinations thereof. The porous layer 150 may include ePTFE (for example, ePTFE as taught in U.S. Pat. No. 6,541,589 to Baille) or other porous expanded and fibrilizing fluoropolymers. The one or more laminate layers 130 having the barrier layer 145 and the porous layer 150 may be constructed by coating or otherwise depositing the fluoropolymer onto the porous layer to create the composite fluoropolymer film. One such example of this would be to deposit granular or powdered fluoropolymers such as powdered PTFE onto a porous ePTFE surface in a coating process. The ePTFE support should be constructed to be thermally stable enough to allow heat treatment of the deposited fluoropolymer for the creation of a barrier or for bonding of the deposited layer to the porous ePTFE support. The ePTFE layer may be filled with an organic or inorganic material to provide color, lubricity, or other functional attributes.

Figure 4:
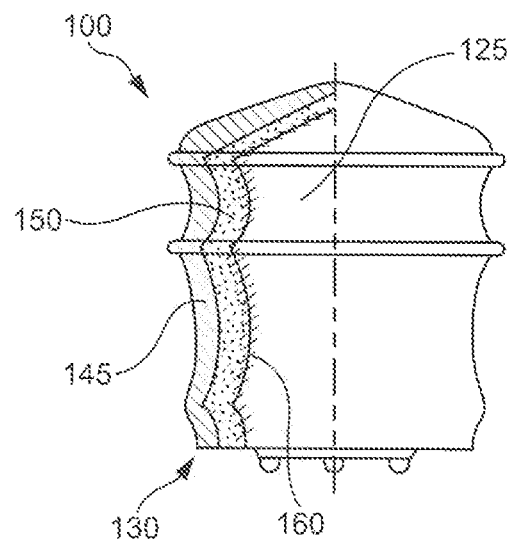

In accordance with some aspects of the present invention, the elastomer material of the elastomeric body 125 may at least partially penetrate the porous layer 150. FIG. 4 illustrates a cross-section of a stopper depicting the barrier layer 145, the porous layer 150, and the elastomeric body 125. Specifically, FIG. 4 shows a region of partial penetration 160 of the elastomer material of the elastomeric body 125 into the porous layer 150. Penetration of the elastomer material of the elastomeric body 125 into the porous layer 150 may improve the bond between the elastomeric body 125 and the one or more laminate layers 130.

Figure 5:
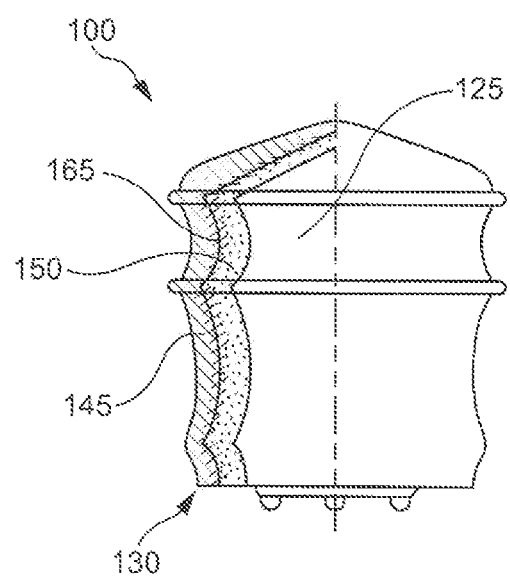

In accordance with other aspects, the material of the barrier layer 145 may at least partially penetrate the porous layer 150. FIG. 5 illustrates a cross-section of a stopper depicting the barrier layer 145, the porous layer 150, and the elastomeric body 125. Specifically, FIG. 5 shows a region of partial penetration 165 of the material of the barrier layer 145 into the porous layer 150. Penetration of the material of the barrier layer 145 into the porous layer 150 may improve the bond between the barrier layer 145 and the porous layer 150. The region of partial penetration 165 may also provide support for the barrier layer 145 to impart strength, toughness, compliance and stability, which may be beneficial in both the forming process and in the application.

Figure 6:
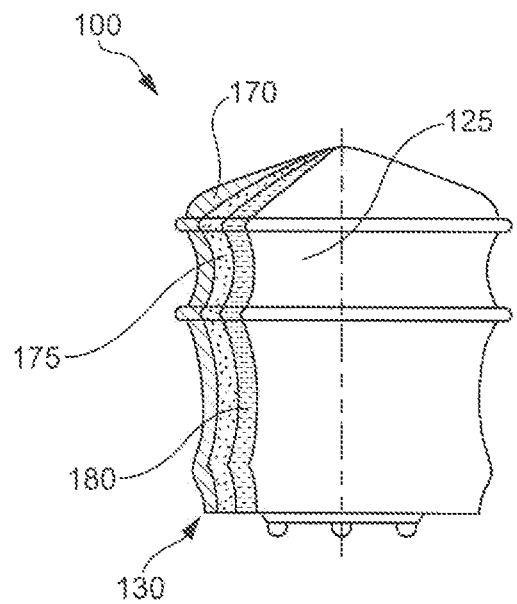

In another embodiment, as shown in FIG. 6, the one or more laminate layers 130 may comprise a composite fluoropolymer film having a densified expanded fluoropolymer layer 170, a barrier melt fluoropolymer layer 175, and a porous layer 180. The densified expanded fluoropolymer layer 170 can may include or be formed of a densified ePTFE. The barrier melt fluoropolymer layer 175 may include a fluoropolymer such as a densified expanded fluoropolymer, PTFE, ePTFE, densified ePTFE, or fluorinated propylene (FEP), polyethylene, polypropylene, polyvinylidene fluoride, polyvinylfluoride, perfluoropropylevinylether, perfluoroalkoxy polymers, and copolymers and combinations thereof. The porous layer 150 may include or be formed of ePTFE or other porous expanded and fibrilizing fluoropolymers. The one or more laminate layers 130 having the densified expanded fluoropolymer layer 170, the barrier melt fluoropolymer layer 175 and the porous layer 180 may be constructed by coating or otherwise depositing the fluoropolymer onto the porous layer to create the composite fluoropolymer film. The densified ePTFE film, fluoropolymer, and porous layer may be thermoformed to make a preform, and may be combined with the elastomeric body 125 by injection molding, compression molding, priming and post laminating around an elastomer perform, or other suitable methods known to the skilled artisan.

Figure 7:
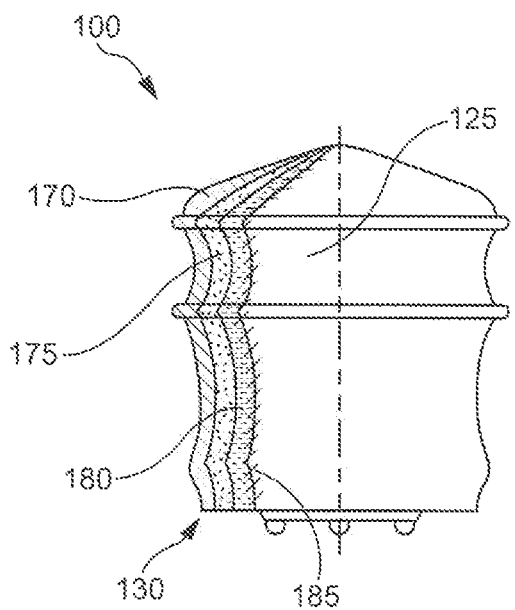

In accordance with some aspects, the elastomer material of the elastomeric body 125 may at least partially penetrate the porous layer 180. FIG. 7 shows a cross-section of a stopper depicting a densified expanded fluoropolymer layer 170, a barrier melt fluoropolymer layer 175, and a porous layer 180. Specifically, FIG. 7 shows a region of partial penetration 185 of the elastomer material of the elastomeric body 125 into the porous layer 180. Penetration of the elastomer material of the elastomeric body 125 into the porous layer 180 may improve the bond between the elastomeric body 125 and the one or more laminate layers 130.

Figure 8:
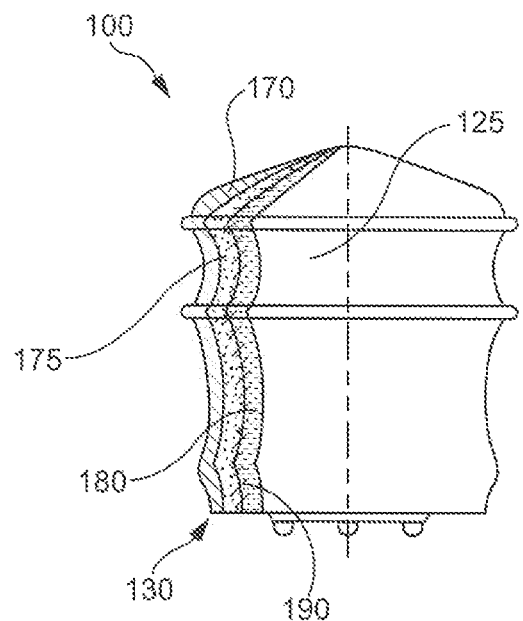

In accordance with other aspects, the material of the barrier melt fluoropolymer layer 175 may at least partially penetrate the porous layer 180. FIG. 8 shows a cross-section of a stopper according to an embodiment depicting densified expanded fluoropolymer layer 170, a barrier melt fluoropolymer layer 175 and a porous layer 180. Specifically, FIG. 8 shows a region of partial penetration 190 of the material of the barrier melt fluoropolymer layer 175 into the porous layer 180. Penetration of the material of the barrier melt fluoropolymer layer 175 into the porous layer 180 may improve the bond between the barrier melt fluoropolymer layer 175 and the porous layer 180. The region of partial penetration 190 may also provide support for the barrier melt fluoropolymer layer 175 to impart strength, toughness, compliance and stability, which is beneficial in both the forming process and in use.

Figure 9:
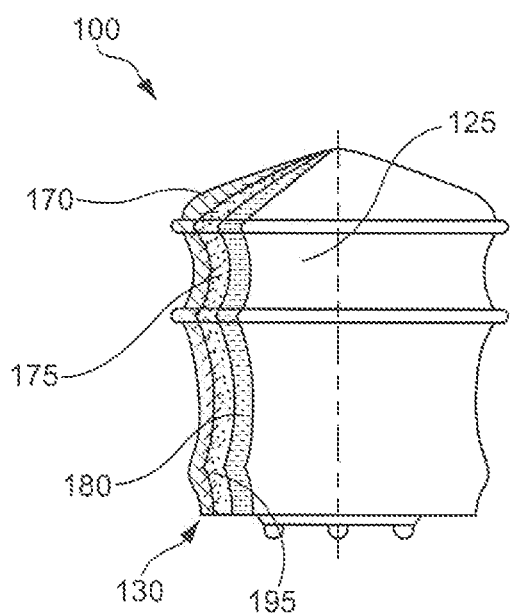

In accordance with some aspects, the material of the barrier melt fluoropolymer layer 175 may at least partially penetrate the densified expanded fluoropolymer layer 170. FIG. 9 shows a cross-section of a stopper depicting a densified expanded fluoropolymer layer 170, a barrier melt fluoropolymer layer 175, and a porous layer 180. Specifically, FIG. 9 shows a region of partial penetration 195 of the material of the barrier melt fluoropolymer layer 175 into the densified expanded fluoropolymer layer 170. Penetration of the material of the barrier melt fluoropolymer layer 175 into the densified expanded fluoropolymer layer 170 may improve the bond between the barrier melt fluoropolymer layer 175 and the densified expanded fluoropolymer layer 170. The region of partial penetration 195 may also provide support for the barrier melt fluoropolymer layer 175 to impart strength, toughness, compliance and stability, which is beneficial in both the forming process and in use.

The stopper 100 may include various degrees of penetration of either the elastomer material or the barrier polymer into the porous material or the densified expanded fluoropolymer layer as shown in FIGS. 4, 5, and 7-9, and as described in U.S. Pat. No. 8,722,178 to Ashmead, et al., U.S. Patent Publication No. 2012/0251748 to Ashmead, et al., and U.S. Patent Publication No. 2016/0022918 to Ashmead, et al. It is to be appreciated that there are many variations of the processes described herein that could be utilized for forming the stopper 100 without departing from the scope and/or spirit the invention. Some of these variations may include, but are not limited to, forming any of the fluoropolymers used in the stopper 100 of the present invention with an expanded fluoropolymer film based on PTFE, modified PTFE, and PTFE and TFE copolymers such as, for example, the resins as described in U.S. Pat. No. 6,541,589 to Baille and U.S. Pat. No. 8,637,144 to Ford.

IV. Stopper Structure

Figure 10A:
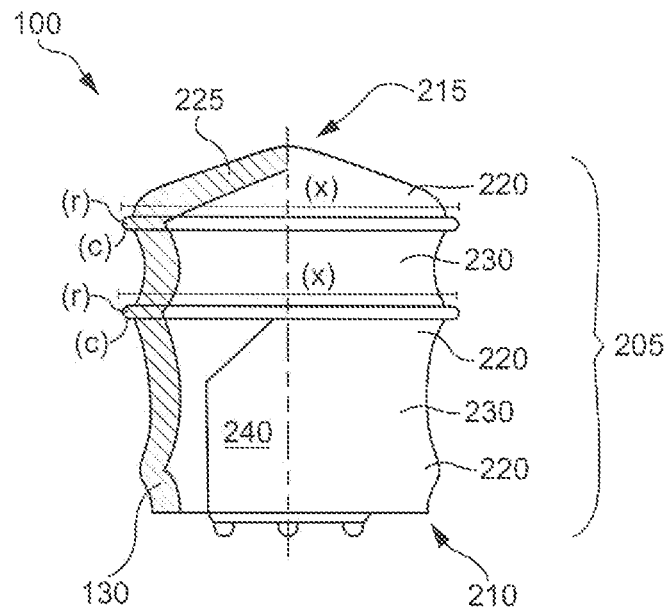
FIG. 10A depicts a cross sectional side view of a non-compressed stopper in accordance with some embodiments.
Figure 10B:
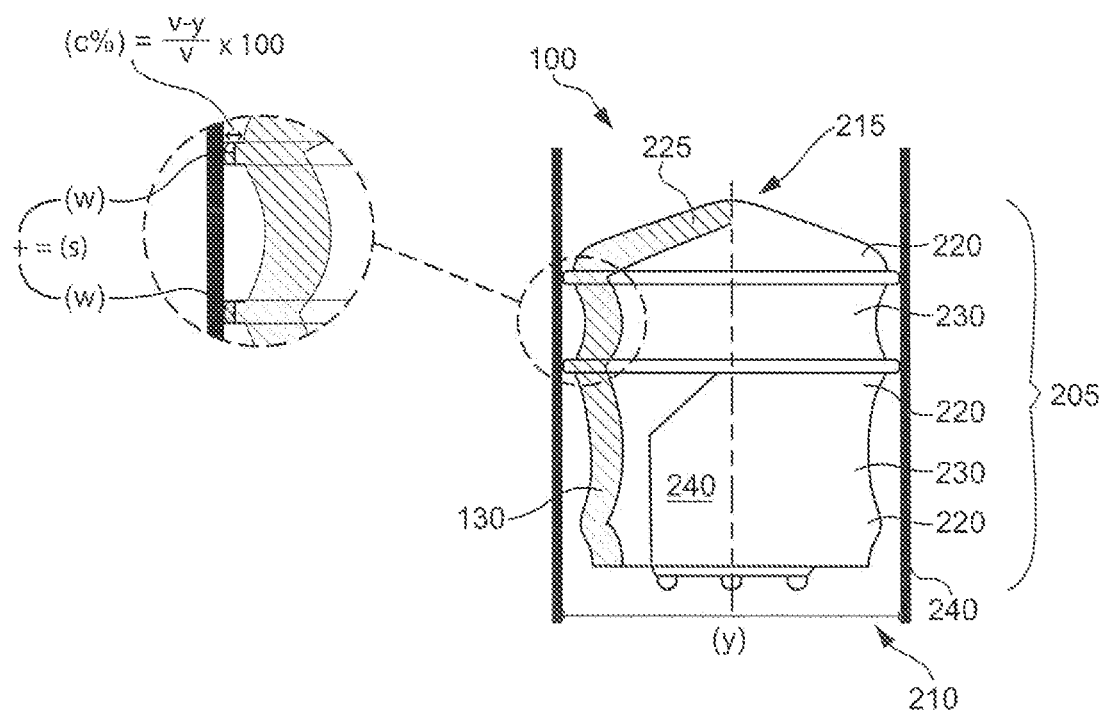
FIG. 10B depicts a cross sectional side view of a compressed stopper in accordance with some embodiments.

In some embodiments, the stopper 100 is configured to achieve container closure integrity with high levels of air and liquid impermeability while also maintaining acceptably low break loose and slide forces. FIGS. 10A and 10B show such a stopper 100 that includes a body 205 having opposed proximal and distal ends 210 and 215 and two or more ribs 220. A head portion 225 is formed integrally with the distal end 215 of the body 205. One or more annular grooves 230 is formed in an outer surface of the body 205, thus forming and connecting the two or more ribs 220. At least one of the two or more ribs 220 is laminated with the one or more laminate layers 130. A cavity 240 may extend from the proximal end of 210 of the body 205 towards the distal end 215. The distal end 90 of the plunger rod 85 may be inserted and fixed inside the cavity 240 of the stopper.

The two or more ribs 220 can be classified based on whether they have a sealing surface or a non-sealing surface. As used herein, the term "sealing surface" refers to a rib having a compressibility of greater than about 7.9%, and the term "non-sealing surface" refers to a rib having a compressibility of about 7.9% or less. For example, the two ribs shown in FIGS. 10A and 10B as being the furthest towards the distal end 215 of the body 205 have a compressibility of greater than about 7.9%, and thus are referred to as having a sealing surface. In contrast, the one rib shown in FIGS. 10A and 10B as being the furthest towards the proximal end 210 of the body 205 has a compressibility of about 7.9% or less, and thus is referred to as having a non-sealing surface. As the skilled artisan will appreciate, although the present invention is described hereafter as it relates to rib arrangement shown in FIGS. 10A and 10B, other types of rib arrangements are contemplated, such as, for example having three ribs with sealing surfaces, without departing from the spirit and scope of the present disclosure.

Each rib 220 having a sealing surface includes at least one a predefined outer diameter (x) measured from an apex of the respective rib with the stopper 100 in a non-compressed state (see, e.g., FIG. 10A), a curvature (c) having a predefined radius of curvature (r) at the apex of the respective rib that is measured with the stopper 100 in a non-compressed state (see, e.g., FIG. 10A), and a contact width (w) between each respective rib and an inner surface 240 of the barrel measured at a compressibility (C %) of the stopper 100 in a compressed state (see, e.g., FIG. 10B). In some embodiments, at least one of: the predefined outer diameter (x) of at least one rib 220 having a sealing surface is greater than about 5.0 mm, between about 5.0 mm and about 14.0 mm, or between about 5.5 mm and about 10 mm. In some embodiments, the predefined outer diameter (x) may be, for example, about 7.42 mm or about 5.5 mm. The predefined radius of curvature (r) of at least one rib 220 having a sealing surface is less than about 0.22 mm, between about 0.05 mm and about 0.20 mm, or between about 0.12 mm and about 0.17 mm. The contact width (w) of at least one rib 220 having a sealing surface measured at the compressibility (C %) is less than about 1.0 mm. In some embodiments, the contact width at the compressibility is between about 0.05 mm and about 1.0 mm, between about 0.1 and about 0.75 mm, or between about 0.2 and about 0.5 mm. A sliding surface (S) of the stopper 100 includes a sum of the contact widths (w) of all the ribs having a sealing surface that is less than 2.0 mm. The sliding surface may be less than about 2.0 mm, or between about 0.05 mm and about 1.9 mm, between about 0.1 mm and about 1.65 mm, or between about 0.5 mm and about 1.25 mm.

As the skilled artisan will appreciate, the ribs 220 can be structured in any number of configurations, and FIGS. 10A and 10B are provided for purposes of illustration only, and are not intended to limit the present disclosure. For example, in certain embodiments, all of the ribs 220 having a sealing surface may have a same predefined outer diameter (x). In other embodiments, each rib 220 having a sealing surface may have its own predefined outer diameter (x). For example, a distal or leading rib may have a predefined outer diameter (1x) and a proximal or trailing rib may have a predefined outer diameter (2x) that is between about 75% and about 99.9% of the predefined outer diameter (1x).

The compressibility (C %) is defined in relation to a maximum outer diameter (v) of the ribs 220 having a sealing surface of the stopper 100 in a non-compressed state and the inner diameter (y) of the inner surface 240 of the barrel as follows: C %=((v−y)/v)×100. For example, understanding that each of the ribs 220 having a sealing surface may have its own predefined outer diameter (x), and thus its own compression, compressibility (C %) of the stopper 100 is defined in relation to the largest outer diameter (x) (i.e., the maximum outer diameter (v)) out of all of the ribs 220 having a sealing surface of the stopper 100 in a non-compressed state. In some embodiments, the maximum outer diameter (v) of the ribs 220 having a sealing surface is greater than about 5.0 mm, between about 5.0 mm and about 14.0 mm, or between about 5.5 mm and about 10 mm. In some embodiments, the sealing surface may be, for example, about 7.42 mm or about 5.5 mm; the inner diameter (y) may be between about 2.5 mm and about 30.0 mm, between about 4.5 mm and about 20.0 mm, or between about 5.5 mm and about 11.5 mm. In some embodiment, the inner diameter may be, for example, about 6.35 mm or nominally (a tolerance of +/−0.1 on the 4.65 side and a tolerance of +/−0.2 on the 11.85) between about 4.65 mm and about 11.85 mm; and the compressibility (C %) of the stopper may be greater than about 7.9%, between about 9.5% and about 20.0%, or between about 11.75% and about 18.5%. In some embodiments, the compressibility may be, for example, about 14.4%. In some embodiments, a ratio of the maximum outer diameter (v) of the ribs 220 having a sealing surface to the inner diameter (y) of the inner surface 240 of the barrel may be greater than, for example, about 1.08, or between about 1.10 and about 1.25, or between about 1.13 and about 1.23.

In some embodiments, the stopper 100 may be configured based on the aforementioned composition of the one or more laminate layers 130 and properties of the two or more ribs 220 to have a predetermined slide force and predetermined seal pressure. In some embodiments, the predetermined slide force is a peak extrusion force of less than about 20 N at speeds of 50-250 mm/min using a syringe filled with water. In some embodiments, the predetermined seal pressure is a seal pressure adequate to achieve a helium leak rate of less than $6\times10^{-6}$ sccs.

Referring to FIGS. 10A and 10B, it was found that the seal pressure of a stopper laminated with a fluoropolymer film that is in contact with a hydrophilic or lubricant free inner surface of a barrel depends particularly upon compressibility (C %), and the break loose (e.g., the amount of force required to begin moving the stopper from a stationary position within the barrel) and slide forces (e.g., the amount of force required to move the stopper parallel along the inner surface of the barrel) particularly depend upon the contact width (w) or sliding surface (S). Additionally, it was found that distortion of the fluoropolymer film (both the portion of the fluoropolymer film contacting the inner surface of the barrel and the portion of the fluoropolymer film not contacting the inner surface of the barrel) of the stopper that is in contact with a hydrophilic or lubricant free inner surface of a barrel depends particularly upon the dimensions of the two or more ribs. Some of the conventional stoppers laminated with a fluoropolymer film when compressed enough to achieve a desired seal pressure have unacceptable break loose and slide forces due to excessive contact area or sliding surface between the stopper and the inner surface of barrel. Moreover, some conventional laminates tends to distort during movement of the plunger rod within the barrel during charging or discharging due to the structure of the one or more annular grooves and the two or more ribs.

However, it has been surprisingly and unexpectedly found that when the contact width (w) of at least one rib with a sealing surface measured at a compressibility (C %) of greater than 7.9% is less than about 1.0 mm, or between about 0.05 mm and about 1.0 mm, between about 0.1 and about 0.75 mm, or between about 0.2 mm and about 0.5 mm and a sliding surface (S) of the stopper 100 that includes a sum of the contact widths (w) of all the ribs having a sealing surface is less than about 2.0 mm, or between about 0.05 mm and about 1.9 mm, between about 0.1 mm and about 1.65 mm, or between about 0.5 and about 1.25 mm, the stoppers of the present disclosure achieve a desired seal pressure with acceptable break loose and slide forces. Moreover, it has been surprisingly and unexpectedly found that when the predefined radius of curvature (r) of at least one rib having a sealing surface is at less than about 0.22 mm, or between about 0.05 and about 0.20 mm, or between about 0.12 and about 0.17 mm, and the ratio of the maximum outer diameter (v) of at least one rib having a sealing surface to the inner diameter (y) of the inner surface of the barrel is greater than about 1.08, between about 1.10 and about 1.25, or between about 1.13 and about 1.23, the fluoropolymer laminate of the stoppers do not distort under the compressibility (C %), which is necessary to achieve an adequate seal pressure while allowing for acceptably low break loose and slide forces.

Additionally, it has been surprisingly and unexpectedly found that using the aforementioned one or more laminate layers allows for improved geometry with respect to aforementioned properties of the two or more ribs without causing leak paths. Accordingly, the aforementioned aspects of the present invention allow for the construction of stoppers laminated with a fluoropolymer film that achieve sufficient contact with the inner surface of the barrel of a glass or resin syringe (hydrophilic and/or lubricant free) to achieve high levels of air and liquid impermeability while also maintaining acceptably low break loose and slide forces (i.e., low-friction slidability) but not so much contact that the fluoropolymer film surface is distorted to create leak paths that decrease the air and liquid impermeability.

In another aspect, the medical delivery device, plunger rod, and stopper described herein may be used in combination different therapeutic compounds such as, for example, drugs and biologics, including but not limited to, antibodies, antisense, RNA interference, gene therapy, primary and embryonic stem cells, vaccines, and combinations thereof. For instance, the embodiments described herein may be utilized in combination with any or all of the following:

Cell therapy using cells that are derived primarily from endoderm such as Exocrine secretory epithelial cells and Hormone-secreting cells; ectoderm such as Keratinizing epithelial cells, Wet stratified barrier epithelial cells, Sensory transducer cells, Autonomic neuron cells, Sense organ and peripheral neuron supporting cells, Central nervous system neurons and glial cells, Lens cells; mesoderm such as Metabolism and storage cells, Barrier function cells (lung, gut, exocrine glands, and urogenital tract), Extracellular matrix cells, Contractile cells, Blood and immune system cells, Germ cells, Nurse cell, Interstitial cells or a combination thereof. Additionally cells that are genetically, chemically or physically altered or modified are considered to be in the scope of the invention.

Examples of Exocrine secretory epithelial cells include, but are not limited to, Salivary gland mucous cell, Salivary gland number 1, Von Ebner's gland cell in tongue, Mammary gland cell, Lacrimal gland cell, Ceruminous gland cell in ear, Eccrine sweat gland dark cell, Eccrine sweat gland clear cell, Apocrine sweat gland cell, Gland of Moll cell in eyelid, Sebaceous gland cell, Bowman's gland cell in nose, Brunner's gland cell in duodenum, Seminal vesicle cell, Prostate gland cell, Bulbourethral gland cell, Bartholin's gland cell, Gland of Littre cell, Uterus endometrium cell, Isolated goblet cell of respiratory and digestive tracts, Stomach lining mucous cell, Gastric gland zymogenic cell, Gastric gland oxyntic cell, Pancreatic acinar cell, Paneth cell of small intestine, Type II pneumocyte of lung, Clara cell of lung; Hormone-secreting cells including but not limited to: Anterior pituitary cells, Intermediate pituitary cell, Magnocellular neurosecretory cells, Gut and respiratory tract cells, Thyroid gland cells, Parathyroid gland cells, Adrenal gland cells, Leydig cell of testes secreting testosterone, Theca interna cell of ovarian follicle secreting estrogen, Corpus luteum cell of ruptured ovarian follicle secreting progesterone, Juxtaglomerular cell, Macula densa cell of kidney, Peripolar cell of kidney, Mesangial cell of kidney, Pancreatic islets; Keratinizing epithelial cells including but not limited to: Epidermal keratinocyte, Epidermal basal cell, Keratinocyte of fingernails and toenails, Nail bed basal cell, Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell; Wet stratified barrier epithelial cells including but not limited to: Surface epithelial cell of stratified squamous epithelium and basal cell of epithelia of cornea, tongue, oral cavity, esophagus, anal canal, distal urethra and vagina, Urinary epithelium cell; Sensory transducer cells including but not limited to: Auditory inner hair cell of organ of Corti, Auditory outer hair cell of organ of Corti, Basal cell of olfactory epithelium, Cold-sensitive primary sensory neurons, Heat-sensitive primary sensory neurons, Merkel cell of epidermis, Olfactory receptor neuron, Pain-sensitive primary sensory neurons, Photoreceptor cells of retina in eye: Proprioceptive primary sensory neurons, Touch-sensitive primary sensory neurons, Type I carotid body cell, Type II carotid body cell, Type I hair cell of vestibular system of ear, Type II hair cell of vestibular system of ear, Type I taste bud cell; Autonomic neuron cells including but not limited to: Cholinergic neural cell, Adrenergic neural cell, Peptidergic neural cell; Sense organ and peripheral neuron supporting cells including but not limited to: Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Taste bud supporting cell, Olfactory epithelium supporting cell, Schwann cell, Satellite glial cell, Enteric glial cell; Central nervous system neurons and glial cells including but not limited to: Astrocyte, Neuron cells, Oligodendrocyte, Spindle neuron; Lens cells including but not limited to: Anterior lens epithelial cell, Crystallin-containing lens fiber cell; Metabolism and storage cells including but not limited to: Adipocytes: Liver lipocyte; Barrier function cells including but not limited to: Kidney parietal cell, Kidney glomerulus podocyte, Kidney proximal tubule brush border cell, Loop of Henle thin segment cell, Kidney distal tubule cell, Kidney collecting duct cell, Principal cells, Intercalated cells, Type I pneumocyte, Pancreatic duct cell, Nonstriated duct cell, Principal cell, Intercalated cell, Duct cell, Intestinal brush border cell, Exocrine gland striated duct cell, Gall bladder epithelial cell, Ductulus efferens nonciliated cell, Epididymal principal cell, Epididymal basal cell; Extracellular matrix cells including but not limited to: Ameloblast epithelial cell, Planum semilunatum epithelial cell of vestibular system of ear, Organ of Corti interdental epithelial cell, Loose connective tissue fibroblasts, Corneal fibroblasts, Tendon fibroblasts, Bone marrow reticular tissue fibroblasts, Other nonepithelial fibroblasts, Pericyte, Nucleus pulposus cell of intervertebral disc, Cementoblast/cementocyte, Odontoblast/odontocyte, Hyaline cartilage chondrocyte, Fibrocartilage chondrocyte, Elastic cartilage chondrocyte, Osteoblast/osteocyte, Osteoprogenitor cell, Hyalocyte of vitreous body of eye, Stellate cell of perilymphatic space of ear, Hepatic stellate cell, Pancreatic stelle cell; Contractile cells including but not limited to: Skeletal muscle cell, Satellite cell, Heart muscle cells, Smooth muscle cell, Myoepithelial cell of iris, Myoepithelial cell of exocrine glands; Blood and immune system cells including but not limited to: Erythrocyte, Megakaryocyte, Monocyte, Connective tissue macrophage, Epidermal Langerhans cell, Osteoclast, Dendritic cell, Microglial cell, Neutrophil granulocyte, Eosinophil granulocyte, Basophil granulocyte, Hybridoma cell, Mast cell, Helper T cell, Suppressor T cell, Cytotoxic T cell, Natural Killer T cell, B cell, Natural killer cell, Reticulocyte, Stem cells and committed progenitors for the blood and immune system; Germ cells including but not limited to: Oogonium/Oocyte, Spermatid, Spermatocyte, Spermatogonium cell, Spermatozoon; Nurse cell including but not limited to: Ovarian follicle cell, Sertoli cell, Thymus epithelial cell; Interstitial cells including but not limited to: Interstitial kidney cells and a combination thereof.

Examples of antibodies, antisense, RNA interference, or gene therapy made to protein targets or gene(s) of: Ataxia Telangiectasia Mutated, Tumor Protein p53, Checkpoint kinase 2, breast cancer susceptibility protein, Double-strand break repair protein, DNA repair protein RAD50, Nibrin, p53-binding protein, Mediator of DNA damage checkpoint protein, H2A histone family member X, Microcephalin, C-term inal-binding protein 1, Structural maintenance of chromosomes protein 1A; Esterases; Phosphatases; Examples of Ion channels include but are not limited to: ligand-gated ion channels, voltage-gated ion channels; Examples of growth factors include but are not limited to: nerve growth factor (NGF), vascular endothelial growth factor (VEGF), platelet-derived growth factor (PDGF), C-fos-induced growth factor (FIGF), platelet-activating factor (PAF), transforming growth factor beta (TGF-β), b, one morphogenetic proteins (BMPs), Activin, inhibin, fibroblast growth factors (FGFs), granulocyte-colony stimulating factor (G-CSF), granulocyte-macrophage colony stimulating factor (GM-CSF), glial cell line-derived neurotrophic factor (GDNF), growth differentiation factor-9 (GDF9), epidermal growth factor (EGF), transforming growth factor-α (TGF-α), growth factor (KGF), migration-stimulating factor (MSF), hepatocyte growth factor-like protein (HGFLP), hepatocyte growth factor (HGF), hepatoma-derived growth factor (HDGF), Insulin-like growth factors; Examples of G Protein-Coupled Receptors (GPCR) include but are not limited to: Adenosine receptor family, Adrenergic receptor family, Angiotensin II receptor, Apelin receptor, Vasopressin receptor family, Brain-specific angiogenesis inhibitor family, Bradykinin receptor family, Bombesin receptor family, Complement component 3a receptor 1, Complement component 5a receptor 1, Calcitonin receptor family, Calcitonin receptor-like family, Calcium-sensing receptor, Cholecystokinin A receptor (CCK1), Cholecystokinin B receptor (CCK2), Chemokine (C-C motif) receptor family, Sphingosine 1-phosphate receptor family, Succinic receptor, Cholinergic receptor family. Chemokine-like receptor family, Cannabinoid receptor family, Corticotropin releasing hormone receptor family, prostaglandin D2 receptor, Chemokine C-X3-C receptor family, Chemokine (C-X-C motif) receptor family, Burkitt lymphoma receptor, Chemokine (C-X-C motif) receptor family, Cysteinyl leukotriene receptor 2 (CYSLT2), chemokine receptor (FY), Dopamine receptor family, G protein-coupled receptor 183 (GPR183), Lysophosphatidic acid receptor family, Endothelin receptor family, Coagulation factor II (thrombin) receptor family, Free fatty acid receptor family, Formylpeptide receptor family, Follicle stimulating hormone receptor (FSHR), gamma-aminobutyric acid (GABA) B receptor, Galanin receptor family, Glucagon receptor, Growth hormone releasing hormone receptor (GHRH), Ghrelin receptor (ghrelin), Growth hormone secretagogue receptor 1b (GHSR1b), Gastric inhibitory polypeptide receptor (GIP), Glucagon-like peptide receptor family, Gonadotropin-releasing hormone receptor (GnRH), pyroglutamylated RFamide peptide receptor (QRFPR), G protein-coupled bile acid receptor 1 (GPBA), Hydroxycarboxylic acid receptor family, Lysophosphatidic acid receptor 4 (LPA4) Lysophosphatidic acid receptor 5 (GPR92), G protein-coupled receptor 79 pseudogene (GPR79), Hydroxycarboxylic acid receptor 1 (HCA1), G-protein coupled receptor (C5L2, FFA4, FFA4, FFA4, GPER, GPR1, GPR101, GPR107, GPR119, GPR12, GPR123, GPR132, GPR135, GPR139, GPR141, GPR142, GPR143, GPR146, GPR148, GPR149, GPR15, GPR150, GPR151, GPR152, GPR157, GPR161, GPR162, GPR17, GPR171, GPR173, GPR176, GPR18, GPR182, GPR20, GPR22, GPR25, GPR26, GPR27, GPR3, GPR31, GPR32, GPR35, GPR37L1, GPR39, GPR4, GPR45, GPR50, GPR52, GPR55, GPR6, GPR61, GPR65, GPR75, GPR78, GPR83, GPR84, GPR85, GPR88, GPR97, TM7SF1), Metabotropic glutamate receptor family, Gastrin releasing peptide receptor (BB2), Orexin receptor family, Histamine receptor family, 5-hydroxytryptamine receptor family, KISS1-derived peptide receptor (kisspeptin), Leucine-rich repeat-containing G protein-coupled receptor family, horiogonadotropin receptor (LH), Leukotriene B4 receptor (BLT1), Adenylate Cyclase Activating Polypeptide 1 Receptor 1 (mPAC1), Motilin receptor, Melanocortin receptor family, Melanin concentrating hormone receptor 1 (MCH1), Neuropeptide Y1 receptor (Y1), Neuropeptide Y2 receptor (NPY2R), Opioid receptor family, Oxytocin recepter (OT), P2Y Purinoceptor 12 (mP2Y12), P2Y Purinoceptor 6 (P2Y6), Pancreatic polypeptide receptor family, Platelet-activating factor receptor family, Prostaglandin E receptor family, Prostanoid IP1 receptor (IP1), MAS-related GPR, member family, Rhodopsin (Rhodopsin), Relaxin family peptide receptor family, Somatostatin receptor family, Tachykinin receptor family, Melatonin receptor family, Urotensin receptor family, Vasoactive intestinal peptide receptor 1 (mVPAC1), Neuromedin B Receptor (BB1), Neuromedin U receptor 1 (NMU1), Neuropeptides B/W receptor family, Neuropeptide FF receptor 1 (NPFF1), neuropeptide S receptor 1 (NPS receptor), Neuropeptide Y receptor family, Neurotensin receptor 1 (NTS1), Opsin 5 (OPNS), Opioid receptor-like receptor (NOP), Oxoeicosanoid (OXE) receptor 1 (OXE), Oxoglutarate (alpha-ketoglutarate) receptor 1 (OXGR1), Purinergic receptor family, Pyrimidinergic receptor family, Prolactin releasing hormone receptor (PRRP), Prokineticin receptor family, Platelet activating receptor (PAF), Prostaglandin F receptor family, Prostaglandin I2 (prostacyclin) receptor family, Parathyroid hormone receptor family, muscarinic 4 (rM4), Prostanoid DP2 receptor (rGPR44), Prokineticin receptor family, Relaxin family peptide receptor family, Secretin receptor (secretin), Smoothened, Frizzled class receptor (Smoothened), trace amine associated receptor family, Tachykinin family, Thromboxane A2 receptor (TP), Thyrotropin-releasing hormone receptor (TRH1), Thyroid Stimulating Hormone Receptor (TSH); Examples of Protein kinases include but are not limited to: AP2 associated kinase, *Homo sapiens* ABL proto-oncogene 1-non-receptor tyrosine-protein kinase family, c-abl oncogene 1 receptor tyrosine kinase family, v-abl Abelson murine leukemia viral oncogene homolog 2, activin A receptor family, chaperone-ABC1 activity of bc1 complex homolog (*S. pombe*) (ADCK3), aarF domain containing kinase 4 (ADCK4), v-akt murine thymoma viral oncogene homolog family, anaplastic lymphoma receptor tyrosine kinase family, protein kinase A family, protein kinase B family, ankyrin repeat and kinase domain containing 1 (ANKK1), NUAK family-SNF1-like kinase, mitogen-activated protein kinase kinase kinase family aurora kinase A (AURKA), aurora kinase B (AURKB), aurora kinase C (AURKC), AXL receptor tyrosine kinase (AXL), BMP2 inducible kinase (BIKE), B lymphoid tyrosine kinase (BLK), bone morphogenetic protein receptor family, BMX non-receptor tyrosine kinase (BMX), v-raf murine sarcoma viral oncogene homolog B1 (BRAF), protein tyrosine kinase 6 (BRK), BR serine/threonine kinase family, Bruton agammaglobulinemia tyrosine kinase (BTK), calcium/calmodulin-dependent protein kinase family, cyclin-dependent kinase family, cyclin-dependent kinase-like family, CHK1 checkpoint homolog (*S. pombe*) (CHEK1), CHK2 checkpoint homolog (*S. pombe*) (CHEK2), Insulin receptor, isoform A (INSR), Insulin receptor, isoform B (INSR), rho-interacting serine/threonine kinase (CIT), v-kit Hardy-Zuckerman 4 feline sarcoma viral oncogene homolog (KIT), CDC-Like Kinase family-Hepatocyte growth factor receptor (MET), Proto-oncogene tyrosine-protein kinase receptor, colony-stimulating factor family receptor, c-src tyrosine kinase (CSK), casein kinase family, megakaryocyte-associated tyrosine kinase (CTK), death-associated protein kinase family, doublecortin-like kinase family, discoidin domain receptor tyrosine kinase, dystrophia myotonica-protein kinase (DMPK), dual-specificity tyrosine-(Y)-phosphorylation regulated kinase family, epidermal growth factor receptor family, eukaryotic translation initiation factor 2-alpha kinase 1 (EIF2AK1), EPH receptor family, Ephrin type-A receptor family, Ephrin type-B receptor family, v-erb-b2 erythroblastic leukemia viral oncogene homolog family, mitogen-activated protein kinase family, endoplasmic reticulum to nucleus signaling 1 (ERN1), PTK2 protein tyrosine kinase 2 (FAK), fer (fps/fes related) tyrosine kinase (FER). feline sarcoma oncogene (FES), Fibroblast growth factor receptor family, Gardner-Rasheed feline sarcoma viral (v-fgr) oncogene homolog (FGR), fms-related tyrosine kinase family, Fms-related tyrosine kinase family, fyn-related kinase (FRK), FYN oncogene related to SRC, cyclin G associated kinase (GAK), eukaryotic translation initiation factor 2 alpha kinase, Growth hormone receptor. G protein-coupled receptor kinase 1 (GRK1), G protein-coupled receptor kinase family, glycogen synthase kinase family, germ cell associated 2 (haspin) (HASPIN), Hemopoietic cell kinase (HCK), homeodomain interacting protein kinase family, mitogen-activated protein kinase kinase kinase kinase family, hormonally up-regulated Neu-associated kinase (HUNK), intestinal cell (MAK-like) kinase (ICK), Insulin-like growth factor 1 receptor (IGF1R), conserved helix-loop-helix ubiquitous kinase (IKK-alpha), inhibitor of kappa light polypeptide gene enhancer in B-cells-kinase beta family, insulin receptor (INSR), insulin receptor-related receptor (INSRR), interleukin-1 receptor-associated kinase family, IL2-inducible T-cell kinase (ITK), Janus kinase family, Kinase Insert Domain Receptor, v-kit Hardy-Zuckerman 4 feline sarcoma viral oncogene homolog, lymphocyte-specific protein tyrosine kinase (LCK), LIM domain kinase family, serine/threonine kinase family leucine-rich repeat kinase family, v-yes-1 Yamaguchi sarcoma viral related oncogene homolog (LYN), male germ cell-associated kinase (MAK), MAP/microtubule affinity-regulating kinase family, microtubule associated serine/threonine kinase family, maternal embryonic leucine zipper kinase, c-mer proto-oncogene tyrosine kinase (MERTK), met proto-oncogene (hepatocyte growth factor receptor), MAP kinase interacting serine/threonine kinase family, myosin light chain kinase family, mixed lineage kinase domain-like protein isoform, CDC42 binding protein kinase family, serine/threonine kinase family, macrophage stimulating 1 receptor (c-met-related tyrosine kinase) (MST1R), mechanistic target of rapamycin (serine/threonine kinase) (MTOR), muscle-skeletal-receptor tyrosine kinase (MUSK), myosin light chain kinase family, NIMA (never in mitosis gene a)-related kinase family, serine/threonine-protein kinase NIM1 (NIM1), nemo-like kinase (NLK), oxidative-stress responsive 1 (OSR1), p21 protein (Cdc42/Rac)-activated kinase family, PAS domain containing serine/threonine kinase, Platelet-derived growth factor receptor family, 3-phosphoinositide dependent protein kinase-1 (PDPK1), Calcium-dependent protein kinase 1, phosphorylase kinase gamma family, Phosphatidylinositol 4,5-bisphosphate 3-kinase, phosphoinositide-3-kinase family, phosphatidylinositol 4-kinase family. phosphoinositide kinase, FYVE finger containing, Pim-1 oncogene (PIM1), pim-2 oncogene (PIM2), pim-3 oncogene (PIM3), phosphatidylinositol-4-phosphate 5-kinase family, phosphatidylinositol-5-phosphate 4-kinase family protein kinase, membrane associated tyrosine/threonine 1 (PKMYT1), protein kinase N family, polo-like kinase family, protein kinase C family, protein kinase D family, cGMP-dependent protein kinase family, eukaryotic translation initiation factor 2-alpha kinase 2 (PRKR), X-linked protein kinase (PRKX), Prolactin receptor (PRLR), PRP4 pre-mRNA processing factor 4 homolog B (yeast) (PRP4), PTK2B protein tyrosine kinase 2 beta (PTK2B), SIK family kinase 3 (QSK), v-raf-1 murine leukemia viral oncogene homolog 1 (RAF1), Neurotrophic tyrosine kinase receptor type family, receptor (TNFRSF)-interacting serine-threonine kinase family, dual serine/threonine and tyrosine protein kinase (RIPK5), Rho-associated, coiled-coil containing protein kinase family, c-ros oncogene 1, receptor tyrosine kinase (ROS1), ribosomal protein S6 kinase family, SH3-binding domain kinase 1 (SBK1), serum/glucocorticoid regulated kinase family, Putative uncharacterized serine/threonine-protein kinase (Sugen kinase 110) (SgK110), salt-inducible kinase family, SNF related kinase (SNRK), src-related kinase, SFRS protein kinase family, Spleen tyrosine kinase (SYK), TAO kinase family, TANK-binding kinase 1 (TBK1), tec protein tyrosine kinase (TEC), testis-specific kinase 1 (TESK1), transforming growth factor, beta receptor family, tyrosine kinase with immunoglobulin-like and EGF-like domains 1 (TIE1), TEK tyrosine kinase, endothelial (TIE2), Angiopoietin-1 receptor (Tie2), tousled-like kinase family, TRAF2 and NCK interacting kinase (TNIK), non-receptor tyrosine kinase family, TNNI3 interacting kinase (TNNI3K), transient receptor potential cation channel, testis-specific serine kinase family, TTK protein kinase (TTK), TXK tyrosine kinase (TXK), Tyrosine kinase 2 (TYK2), TYRO3 protein tyrosine kinase (TYRO3), unc-51-like kinase family, phosphatidylinositol 3-kinase, vaccinia related kinase 2 (VRK2), WEE1 homolog family, WNK lysine deficient protein kinase family, v-yes-1 Yamaguchi sarcoma viral oncogene homolog 1 (YES), sterile alpha motif and leucine zipper containing kinase AZK (ZAK), zeta-chain (TCR) associated protein kinase 70 kDa (ZAP70); Examples of nuclear hormone receptors include but are not limited to: Androgen receptor (AR), Estrogen related receptor alpha (ESRRA), Estrogen receptor 1 (ESR1), Nuclear receptor subfamily 1-group H-member 4 (NR1H4), Nuclear receptor subfamily 3-group C-member 1 (glucocorticoid receptor) (NR3C1), Nuclear receptor subfamily 1-group H-member 3 (Liver X receptor α) (NR1H3), Nuclear receptor subfamily 1-group H-member 2 (Liver X receptor β) (NR1H2), Nuclear receptor subfamily 1-group H-member 2 (Liver X receptor β) (NR1H2), Nuclear receptor subfamily 3-group C-member 2 (Mineralcorticoid receptor) (NR3C2), Peroxisome Proliferator Activated Receptor alpha (PPARA), Peroxisome Proliferator Activated Receptor gamma (PPARG), Peroxisome Proliferator Activated Receptor delta (PPARD), Progesterone receptor α (PGR), Progesterone receptor β (PGR), Retinoic acid receptor-alpha (RARA), Retinoic acid receptor-beta (RARB), Retinoid X receptor-alpha (RXRA), Retinoid X receptor-gamma (RXRG), Thyroid hormone receptor-alpha (THRA), Thyroid hormone receptor-beta (THRB), Retinoic acid-related orphan receptor, Liver X receptor, Farnesoid X receptor, Vitamin D receptor, Pregnane X receptor, Constitutive androstane receptor, Hepatocyte nuclear factor 4, Oestrogen receptor, Oestrogen-related receptor, Glucocortioic receptor, Nerve growth factor-induced-B, Germ cell nuclear factor; Examples of Epigenetic targets include but are not limited to: ATPase family AAA domain-containing protein 2 (ATAD2A), ATPase family-AAA domain containing 2B (ATAD2B), ATPase family AAA domain containing-2B (ATAD2B), bromodomain adjacent to zinc finger domain-1A (BAZ1A), bromodomain adjacent to zinc finger domain-1B (BAZ1B), bromodomain adjacent to zinc finger domain-2A (BAZ2A), bromodomain adjacent to zinc finger domain-2A (BAZ2A), bromodomain adjacent to zinc finger domain-2B (BAZ2B), bromodomain-containing protein 1 (BRD1), Bromodomain containing protein 2-1st bromodomain (BRD2), Bromodomain containing protein 2-1st & 2nd bromodomains (BRD2), bromodomain-containing protein 2 isoform 1-bromodomain 2 (BRD2(2)), bromodomain-containing protein 3-bromodomain 1 (BRD3(1)), Bromodomain-containing protein 3-1st bromodomain (BRD3), Bromodomain-containing protein 3-1st & 2nd bromodomains (BRD3), bromodomain-containing protein 3-bromodomain 2 (BRD3(2)), Bromodomain containing protein 4-1st bromodomain (BRD4), bromodomain-containing protein 4 isoform long-bromodomains 1 and 2 (BRD4(1-2)), bromodomain-containing protein 4 isoform long-bromodomain 2 (BRD4(2)), bromodomain-containing protein 4 isoform short (BRD4(full-length-short-iso.)), Bromodomain containing protein 7 (BRD7), bromodomain containing 8-bromodomain 1 (BRD8(1)), bromodomain containing 8-bromodomain 2 (BRD8(2)), bromodomain-containing protein 9 isoform 1 (BRD9), Bromodomain containing testis-specific-1st bromodomain (BRDT), Bromodomain containing testis-specific-1st & 2nd bromodomains (BRDT), bromodomain testis-specific protein isoform b-bromodomain 2 (BRDT (2)), bromodomain and PHD finger containing-1 (BRPF1), bromodomain and PHD finger containing-3 (BRPF3), bromodomain and PHD finger containing-3 (BRPF3), Bromodomain and WD repeat-containing 3-2nd bromodomain (BRWD3(2)), Cat eye syndrome critical region protein 2 (CECR2), CREB binding protein (CREBBP), E1A binding protein p300 (EP300), EP300 (EP300), nucleosome-remodeling factor subunit BPTF isoform 1 (FALZ), Nucleosome-remodeling factor subunit BPT (FALZ), Euchromatic histone-lysine N-methyltransferase 2 (EHMT2), Histone Acetyltransferase-KAT2A (GCN5L2), Euchromatic histone-lysine N-methyltransferase 1 (EHMT1), Histone-lysine N-methyltransferase MLL (MLL), Polybromo 1-1st bromodomain (PB1(1)), Polybromo 1-2nd bromodomain (PB1 (2)), polybromo 1-bromodomain 2 (PBRM1(2)), polybromo 1-bromodomain 5 (PBRM1(5)), Histone acetyltransferase KAT2B (PCAF), PH-interacting protein-1st bromodomain (PHIP(1)), PH-interacting protein-2nd bromodomain (PHIP (2)), Protein kinase C-binding protein 1 (PRKCBP1), Protein arginine N-methyltransferase 3 (PRMT3), SWI/SNF related-matrix associated-actin dependent regulator of chromatin-subfamily a-member 2 (SMARCA2), SWI/SNF related-matrix associated-actin dependent regulator of chromatin-subfamily a-member 4 (SMARCA4), Nuclear body protein-SP110 (SP110), Nuclear body protein-SP140 (SP140), Transcription initiation factor TFIID subunit 1 (TAF1(1-2)), TAF1 RNA polymerase II-TATA box binding protein (TBP)-associated factor-250 kDa-bromodomain 2 (TAF1(2)), Transcription initiation factor TFIID subunit 1-like-1st bromodomain (TAF1L(1)), Transcription initiation factor TFIID subunit 1-like-2nd bromodomain (TAF1L (2)), tripartite motif containing 24 (TRIM24(Bromo.)), tripartite motif containing 24 (TRIM24(PHD-Bromo.)), E3 ubiquitin-protein ligase TRIM33 (TRIM33), tripartite motif containing 33 (TRIM33(PHD-Bromo.)), WD repeat 9-1st bromodomain (WDR9(1)), WD repeat 9-2nd bromodomain (WDR9(2)); membrane transport proteins including but not limited to ATP-binding cassette (ABC) superfamily, solute carrier (SLC) superfamily, multidrug resistance protein 1 (P-glycoprotein), organic anion transporter 1, and protein such as EAAT3, EAAC1, EAAT1, GLUT1, GLUT2, GLUT9, GLUT10, rBAT, AE1, NBC1, KNBC, CHED2, BTR1, NABC1, CDPD, SGLT1, SGLT2, NIS, CHT1, NET, DAT, GLYT2, CRTR, BOAT1, SIT1, XT3, y+LAT1, BAT1, NHERF1, NHE6, ASBT, DMT1, DCT1, NRAMP2, NKCC2, NCC, KCC3, NACT, MCT1, MCT8, MCT12, SLD, VGLUT3, THTR1, THTR2, PIT2, GLVR2, OCTN2, URAT1, NCKX1, NCKX5, CIC, PiC, ANT1, ORNT1, AGC1, ARALAR, Citrin, STLN2, aralar2, TPC, MUP1, MCPHA, CACT, GC1, PHC, DTD, CLD, DRA, PDS, Prestin, TAT1, FATP4, ENT3, ZnT2, ZnT10, AT1, NPT2A, NPT2B, HHRH, CST, CDG2F, UGAT, UGTL, UGALT, UGT1, UGT2, FUCT1, CDG2C, NST, PAT2, G6PT1, SPX4, ZIP4, LIV4, ZIP13, LZT-Hs9, FPN1, MTP1, IREG1, RHAG, AIM1, PCFT, FLVCR1, FLVCR2, RFT1, RFT2, RFT3, OATP1B1, OATP1B3, OATP2A1; structural proteins including but not limited to tubulin, heat shock protein, Microtubule-stabilizing proteins, Oncoprotein 18, stathmin, kinesin-8 and kinesin-14 family, Kip3, Kif18A; proteases including but not limited ADAM (a disintegrin and metalloprotease) family; Other molecule targets in signal transductions include but are not limited to: Cell division cycle 25 homolog A (CDC25A), forkhead box O3 (forkhead box O3), nuclear factor of kappa light polypeptide gene enhancer in B-cells inhibitor, alpha (NFKBIA), nuclear factor (erythroid-derived 2)-like 2 (NFE2L2), Natriuretic peptide receptor A (NPR1), Tumor necrosis factor receptor superfamily, member 11a (TNFRSF11A), v-rel reticuloendotheliosis viral oncogene homolog A (avian) (RELA), Sterol regulatory element binding transcription factor 2 (SREBF2), CREB regulated transcription coactivator 1 (CRTC1), CREB regulated transcription coactivator 2 (CRTC2), X-box binding protein 1 (XBP1), Catenin (cadherin-associated protein), beta 1 (CTNNB1), and combinations thereof.

Examples of known biologics include but are not limited to: Abbosynagis, Abegrin, Actemra, AFP-Cide, Antova, Arzerra, Aurexis, Avastin, Benlysta, Bexxar, Blontress, Bosatria, Campath, CEA-Cide, CEA-Scan, Cimzia, Cyramza, Ektomab, Erbitux, FibriScint, Gazyva, Herceptin, hPAM4-Cide, HumaSPECT, HuMax-CD4, HuMax-EGFr, Humira, HuZAF, Hybri-ceaker, Ilaris, Indimacis-125, Kadcyla, Lemtrada, LeukArrest, LeukoScan, Lucentis, Lymphomun, LymphoScan, LymphoStat-B, MabThera, Mycograb, Mylotarg, Myoscint, NeutroSpec, Numax, Nuvion, Omnitarg, Opdivo, Orthoclone OKT3, OvaRex, Panorex, Prolia, Prostascint, Raptiva, Remicade, Removab, Rencarex, ReoPro, Rexomun, Rituxan, RoActemra, Scintimun, Simponi, Simulect, Soliris, Stelara, Synagis, Tactress, Theracim, Theragyn, Theraloc, Tysabri, Vectibix, Verluma, Xolair, Yervoy, Zenapax, and Zevalin or combinations thereof.

Examples of known Monoclonal antibodies include but are not limited to: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, ALD403, Alemtuzumab, Alirocumab, Altumomab pentetate, Amatuximab, AMG 334, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMA-638, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lambrolizumab, Lampalizumab, Lanadelumab, Landogrozumab, Laprituximab emtansine, LBR-101/PF0442g7429, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, LY2951742, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesidolumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ubliruximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, and Zolimomab aritox or combinations thereof.

Examples of vaccines developed for viral diseases include but are not limited to: Hepatitis A vaccine, Hepatitis B vaccine, Hepatitis E vaccine, HPV vaccine, Influenza vaccine, Japanese encephalitis vaccine, MMR vaccine, MMRV vaccine, Polio vaccine, Rabies vaccine, Rotavirus vaccine, Varicella vaccine, Shingles vaccine, Smallpox vaccine, Yellow Fever vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, Epstein-Barr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans; Examples of bacterial diseases include but are not limited to: Anthrax vaccines, DPT vaccine, Q fever vaccine, Hib vaccine, Tuberculosis (BCG) vaccine, Meningococcal vaccine, Typhoid vaccine, Pneumococcal conjugate vaccine, Pneumococcal polysaccharide vaccine, Cholera vaccine, Caries vaccine, Ehrlichiosis vaccine, Leprosy vaccine, Lyme disease vaccine, *Staphylococcus aureus* vaccine, *Streptococcus pyogenes* vaccine, Syphilis vaccine, Tularemia vaccine, *Yersinia pestis* vaccine; Examples of parasitic diseases include but are not limited to: Malaria vaccine, Schistosomiasis vaccine, Chagas disease vaccine, Hookworm vaccine, Onchocerciasis river blindness vaccine for humans, Trypanosomiasis vaccine, Visceral leishmaniasis vaccine; Examples of non-infectious diseases include but are not limited to: Alzheimer's disease amyloid protein vaccine, Breast cancer vaccine, Ovarian cancer vaccine, Prostate cancer vaccine, Talimogene laherparepvec (T-VEC); also vaccines including but not limited to the following trade names: ACAM2000, ActHIB, Adacel, Afluria, AFLURIA QUADRIVALENT, Agriflu, BCG Vaccine, BEXSERO, Biothrax, Boostrix, Cervarix, Comvax, DAPTACEL, DECAVAC, Engerix-B, FLUAD, Fluarix, Fluarix Quadrivalent, Flublok, Flucelvax, Flucelvax Quadrivalent, FluLaval, FluMist, FluMist Quadrivalent, Fluvirin, Fluzone Quadrivalent, Fluzone, Fluzone High-Dose and Fluzone Intradermal, Gardasil, Gardasil 9, Havrix, Hiberix, Imovax, Infanrix, IPOL, Ixiaro, JE-Vax, KINRIX, Menactra, Menhibrix, Menomune-A/CY/W-135, Menveo, M-M-R II, M-M-Vax, Pediarix, PedvaxHIB, Pentacel, Pneumovax 23, Poliovax, Prevnar, Prevnar 13, ProQuad, Quadracel, Quadrivalent, RabAvert, Recombivax HB, ROTARIX, RotaTeq, TENIVAC, TICE BCG, Tripedia, TRUMENBA, Twinrix, TYPHIM Vi, VAQTA, Varivax, Vaxchora, Vivotif, YF-Vax, Zostavax, and combinations thereof.

Examples of injectable drugs include but are not limited to: Ablavar (Gadofosveset Trisodium Injection), Abarelix Depot, Abobotulinumtoxin A Injection (Dysport), ABT-263, ABT-869, ABX-EFG, Accretropin (Somatropin Injection), Acetadote (Acetylcysteine Injection), Acetazolamide Injection (Acetazolamide Injection), Acetylcysteine Injection (Acetadote), Actemra (Tocilizumab Injection), Acthrel (Corticorelin Ovine Triflutate for Injection), Actummune, Activase, Acyclovir for Injection (Zovirax Injection), [0137], Adacel, Adalimumab, Adenoscan (Adenosine Injection), Adenosine Injection (Adenoscan), Adrenaclick, AdreView (Iobenguane 1123 Injection for Intravenous Use), Afluria, Ak-Fluor (Fluorescein Injection), Aldurazyme (Laronidase), Alglucerase Injection (Ceredase), Alkeran Injection (Melphalan Hcl Injection), Allopurinol Sodium for Injection (Aloprim), Aloprim (Allopurinol Sodium for Injection), Alprostadil, Alsuma (Sumatriptan Injection), ALTU-238, Amino Acid Injections, Aminosyn, Apidra, Apremilast, Alprostadil Dual Chamber System for Injection (Caverject Impulse), AMG 009, AMG 076, AMG 102, AMG 108, AMG 114, AMG 162, AMG 220, AMG 221, AMG 222, AMG 223, AMG 317, AMG 379, AMG 386, AMG 403, AMG 477, AMG 479, AMG 517, AMG 531, AMG 557, AMG 623, AMG 655, AMG 706, AMG 714, AMG 745, AMG 785, AMG 811, AMG 827, AMG 837, AMG 853, AMG 951, Amiodarone HCl Injection (Amiodarone HCl Injection), Amobarbital Sodium Injection (Amytal Sodium), Amytal Sodium (Amobarbital Sodium Injection), Anakinra, Anti-Abeta, Anti-Beta7, Anti-Beta20, Anti-CD4, Anti-CD20, Anti-CD40, Anti-IFNalpha, Anti-IL13, Anti-OX40L, Anti-oxLDS, Anti-NGF, Anti-NRP1, Arixtra, Amphadase (Hyaluronidase Inj), Ammonul (Sodium Phenylacetate and Sodium Benzoate Injection), Anaprox, Anzemet Injection (Dolasetron Mesylate Injection), Apidra (Insulin Glulisine [rDNA origin] Inj), Apomab, Aranesp (darbepoetin alfa), Argatroban (Argatroban Injection), Arginine Hydrochloride Injection (R-Gene 10, Aristocort, Aristospan, Arsenic Trioxide Injection (Trisenox), Articane HCl and Epinephrine Injection (Septocaine), Arzerra (Ofatumumab Injection), Asclera (Polidocanol Injection), Ataluren, Ataluren-DMD, Atenolol Inj (Tenormin I.V. Injection), Atracurium Besylate Injection (Atracurium Besylate Injection), Avastin, Azactam Injection (Aztreonam Injection), Azithromycin (Zithromax Injection), Aztreonam Injection (Azactam Injection), Baclofen Injection (Lioresal Intrathecal), Bacteriostatic Water (Bacteriostatic Water for Injection), Baclofen Injection (Lioresal Intrathecal), Bal in Oil Ampules (Dimercarprol Injection), BayHepB, BayTet, Benadryl, Bendamustine Hydrochloride Injection (Treanda), Benztropine Mesylate Injection (Cogentin), Betamethasone Injectable Suspension (Celestone Soluspan), Bexxar, Bicillin C-R 900/300 (Penicillin G Benzathine and Penicillin G Procaine Injection), Blenoxane (Bleomycin Sulfate Injection), Bleomycin Sulfate Injection (Blenoxane), Boniva Injection (Ibandronate Sodium Injection), Botox Cosmetic (OnabotulinumtoxinA for Injection), BR3-FC, Bravelle (Urofollitropin Injection), Bretylium (Bretylium Tosylate Injection), Brevital Sodium (Methohexital Sodium for Injection), Brethine, Briobacept, BTT-1023, Bupivacaine HCl, Byetta, Ca-DTPA (Pentetate Calcium Trisodium Inj), Cabazitaxel Injection (Jevtana), Caffeine Alkaloid (Caffeine and Sodium Benzoate Injection), Calcijex Injection (Calcitrol), Calcitrol (Calcijex Injection), Calcium Chloride (Calcium Chloride Injection 10%), Calcium Disodium Versenate (Edetate Calcium Disodium Injection), Campath (Altemtuzumab), Camptosar Injection (Irinotecan Hydrochloride), Canakinumab Injection (Ilaris), Capastat Sulfate (Capreomycin for Injection), Capreomycin for Injection (Capastat Sulfate), Cardiolite (Prep kit for Technetium Tc99 Sestamibi for Injection), Carticel, Cathflo, Cefazolin and Dextrose for Injection (Cefazolin Injection), Cefepime Hydrochloride, Cefotaxime, Ceftriaxone, Cerezyme, Carnitor Injection, Caverject, Celestone Soluspan, Celsior, Cerebyx (Fosphenytoin Sodium Injection), Ceredase (Alglucerase Injection), Ceretec (Technetium Tc99m Exametazime Injection), Certolizumab, CF-101, Chloramphenicol Sodium Succinate (Chloramphenicol Sodium Succinate Injection), Chloramphenicol Sodium Succinate Injection (Chloramphenicol Sodium Succinate), Cholestagel (Colesevelam HCL), Choriogonadotropin Alfa Injection (Ovidrel), Cimzia, Cisplatin (Cisplatin Injection), Clolar (Clofarabine Injection), Clomiphine Citrate, Clonidine Injection (Duraclon), Cogentin (Benztropine Mesylate Injection), Colistimethate Injection (Coly-Mycin M), Coly-Mycin M (Colistimethate Injection), Compath, Conivaptan Hcl Injection (Vaprisol), Conjugated Estrogens for Injection (Premarin Injection), Copaxone, Corticorelin Ovine Triflutate for Injection (Acthrel), Corvert (Ibutilide Fumarate Injection), Cubicin (Daptomycin Injection), CF-101, Cyanokit (Hydroxocobalam in for Injection), Cytarabine Liposome Injection (DepoCyt), Cyanocobalamin, Cytovene (ganciclovir), D.H.E. 45, Dacetuzumab, Dacogen (Decitabine Injection), Dalteparin, Dantrium IV (Dantrolene Sodium for Injection), Dantrolene Sodium for Injection (Dantrium IV), Daptomycin Injection (Cubicin), Darbepoietin Alfa, DDAVP Injection (Desmopressin Acetate Injection), Decavax, Decitabine Injection (Dacogen), Dehydrated Alcohol (Dehydrated Alcohol Injection), Denosumab Injection (Prolia), Delatestryl, Delestrogen, Delteparin Sodium, Depacon (Valproate Sodium Injection), Depo Medrol (Methylprednisolone Acetate Injectable Suspension), Depo-Cyt (Cytarabine Liposome Injection), DepoDur (Morphine Sulfate XR Liposome Injection), Desmopressin Acetate Injection (DDAVP Injection), Depo-Estradiol, Depo-Provera 104 mg/ml, Depo-Provera 150 mg/ml, Depo-Testosterone, Dexrazoxane for Injection, Intravenous Infusion Only (Totect), Dextrose/Electrolytes, Dextrose and Sodium Chloride Inj (Dextrose 5% in 0.9% Sodium Chloride), Dextrose, Diazepam Injection (Diazepam Injection), Digoxin Injection (Lanoxin Injection), Dilaudid-HP (Hydromorphone Hydrochloride Injection), Dimercarprol Injection (Bal in Oil Ampules), Diphenhydramine Injection (Benadryl Injection), Dipyridamole Injection (Dipyridamole Injection), DMOAD, Docetaxel for Injection (Taxotere), Dolasetron Mesylate Injection (Anzemet Injection), Doribax (Doripenem for Injection), Doripenem for Injection (Doribax), Doxercalciferol Injection (Hectorol Injection), Doxil (Doxorubicin Hcl Liposome Injection), Doxorubicin Hcl Liposome Injection (Doxil), Duraclon (Clonidine Injection), Duramorph (Morphine Injection), Dysport (Abobotulinumtoxin A Injection), Ecallantide Injection (Kalbitor), EC-Naprosyn (naproxen), Edetate Calcium Disodium Injection (Calcium Disodium Versenate), Edex (Alprostadil for Injection), Engerix, Edrophonium Injection (Enlon), Eliglustat Tartate, Eloxatin (Oxaliplatin Injection), Emend Injection (Fosaprepitant Dimeglumine Injection), Enalaprilat Injection (Enalaprilat Injection), Enlon (Edrophonium Injection), Enoxaparin Sodium Injection (Lovenox), Eovist (Gadoxetate Disodium Injection), Enbrel (etanercept), Enoxaparin, Epicel, Epinepherine, Epipen, Epipen Jr., Epratuzumab, Erbitux, Ertapenem Injection (Invanz), Erythropoieten, Essential Amino Acid Injection (Nephramine), Estradiol Cypionate, Estradiol Valerate, Etanercept, Exenatide Injection (Byetta), Evlotra, Fabrazyme (Adalsidase beta), Famotidine Injection, FDG (Fludeoxyglucose F 18 Injection), Feraheme (Ferumoxytol Injection), Feridex I.V. (Ferumoxides Injectable Solution), Fertinex, Ferumoxides Injectable Solution (Feridex I.V.), Ferumoxytol Injection (Feraheme), Flagyl Injection (Metronidazole Injection), Fluarix, Fludara (Fludarabine Phosphate), Fludeoxyglucose F 18 Injection (FDG), Fluorescein Injection (Ak-Fluor), Follistim AQ Cartridge (Follitropin Beta Injection), Follitropin Alfa Injection (Gonal-f RFF), Follitropin Beta Injection (Follistim AQ Cartridge), Folotyn (Pralatrexate Solution for Intravenous Injection), Fondaparinux, Forteo (Teriparatide (rDNA origin) Injection), Fostamatinib, Fosaprepitant Dimeglumine Injection (Emend Injection), Foscarnet Sodium Injection (Foscavir), Foscavir (Foscarnet Sodium Injection), Fosphenytoin Sodium Injection (Cerebyx), Fospropofol Disodium Injection (Lusedra), Fragm in, Fuzeon (enfuvirtide), GA101, Gadobenate Dimeglumine Injection (Multihance), Gadofosveset Trisodium Injection (Ablavar), Gadoteridol Injection Solution (ProHance), Gadoversetamide Injection (OptiMARK), Gadoxetate Disodium Injection (Eovist), Ganirelix (Ganirelix Acetate Injection), Gardasil, GC1008, GDFD, Gemtuzumab Ozogamicin for Injection (Mylotarg), Genotropin, Gentamicin Injection, GENZ-112638, Golimumab Injection (Simponi Injection), Gonal-f RFF (Follitropin Alfa Injection), Granisetron Hydrochloride (Kytril Injection), Gentamicin Sulfate, Glatiramer Acetate, Glucagen, Glucagon, HAE1, Haldol (Haloperidol Injection), Havrix, Hectorol Injection (Doxercalciferol Injection), Hedgehog Pathway Inhibitor, Heparin, Herceptin, hG-CSF, Humalog, Human Growth Hormone, Humatrope, HuMax, Humegon, Humira, Humulin, Ibandronate Sodium Injection (Boniva Injection), Ibuprofen Lysine Injection (NeoProfen), Ibutilide Fumarate Injection (Corvert), Idamycin PFS (Idarubicin Hydrochloride Injection), Idarubicin Hydrochloride Injection (Idamycin PFS), Ilaris (Canakinumab Injection), Imipenem and Cilastatin for Injection (Primaxin I.V.), Imitrex, Incobotulinumtoxin A for Injection (Xeomin), Increlex (Mecasermin [rDNA origin] Injection), Indocin IV (Indomethacin Inj), Indomethacin Inj (Indocin IV), Infanrix, Innohep, Insulin, Insulin Aspart [rDNA origin] Inj (NovoLog), Insulin Glargine [rDNA origin] Injection (Lantus), Insulin Glulisine [rDNA origin] Inj (Apidra), Interferon alfa-2b, Recombinant for Injection (Intron A), Intron A (Interferon alfa-2b, Recombinant for Injection), Invanz (Ertapenem Injection), Invega Sustenna (Paliperidone Palmitate Extended-Release Injectable Suspension), Invirase (saquinavir mesylate), Iobenguane 1123 Injection for Intravenous Use (AdreView), Iopromide Injection (Ultravist), Ioversol Injection (Optiray Injection), Iplex (Mecasermin Rinfabate [rDNA origin] Injection), Iprivask, Irinotecan Hydrochloride (Camptosar Injection), Iron Sucrose Injection (Venofer), Istodax (Romidepsin for Injection), Itraconazole Injection (Sporanox Injection), Jevtana (Cabazitaxel Injection), Jonexa, Kalbitor (Ecallantide Injection), KCL in D5NS (Potassium Chloride in 5% Dextrose and Sodium Chloride Injection), KCL in D5W, KCL in NS, Kenalog 10 Injection (Triamcinolone Acetonide Injectable Suspension), Kepivance (Paliferm in), Keppra Injection (Levetiracetam), Keratinocyte, KFG, Kinase Inhibitor, Kineret (Anakinra), Kinlytic (Urokinase Injection), Kinrix, Klonopin (clonazepam), Kytril Injection (Granisetron Hydrochloride), lacosamide Tablet and Injection (Vimpat), Lactated Ringer's, Lanoxin Injection (Digoxin Injection), Lansoprazole for Injection (Prevacid I.V.), Lantus, Leucovorin Calcium (Leucovorin Calcium Injection), Lente (L), Leptin, Levemir, Leukine Sargramostim, Leuprolide Acetate, Levothyroxine, Levetiracetam (Keppra Injection), Lovenox, Levocarnitine Injection (Carnitor Injection), Lexiscan (Regadenoson Injection), Lioresal Intrathecal (Baclofen Injection), Liraglutide [rDNA] Injection (Victoza), Lovenox (Enoxaparin Sodium Injection), Lucentis (Ranibizumab Injection), Lumizyme, Lupron (Leuprolide Acetate Injection), Lusedra (Fospropofol Disodium Injection), Maci, Magnesium Sulfate (Magnesium Sulfate Injection), Mannitol Injection (Mannitol IV), Marcaine (Bupivacaine Hydrochloride and Epinephrine Injection), Maxipime (Cefepime Hydrochloride for Injection), MDP Multidose Kit of Technetium Injection (Technetium Tc99m Medronate Injection), Mecasermin [rDNA origin] Injection (Increlex), Mecasermin Rinfabate [rDNA origin] Injection (Iplex), Melphalan Hcl Injection (Alkeran Injection), Methotrexate, Menactra, Menopur (Menotropins Injection), Menotropins for Injection (Repronex), Methohexital Sodium for Injection (Brevital Sodium), Methyldopate Hydrochloride Injection, Solution (Methyldopate Hcl), Methylene Blue (Methylene Blue Injection), Methylprednisolone Acetate Injectable Suspension (Depo Medrol), MetMab, Metoclopramide Injection (Reglan Injection), Metrodin (Urofollitropin for Injection), Metronidazole Injection (Flagyl Injection), Miacalcin, Midazolam (Midazolam Injection), Mimpara (Cinacalet), Minocin Injection (Minocycline Inj), Minocycline Inj (Minocin Injection), Mipomersen, Mitoxantrone for Injection Concentrate (Novantrone), Morphine Injection (Duramorph), Morphine Sulfate XR Liposome Injection (DepoDur), Morrhuate Sodium (Morrhuate Sodium Injection), Motesanib, Mozobil (Plerixafor Injection), Multihance (Gadobenate Dimeglumine Injection), Multiple Electrolytes and Dextrose Injection, Multiple Electrolytes Injection, Mylotarg (Gemtuzumab Ozogamicin for Injection), Myozyme (Alglucosidase alfa), Nafcillin Injection (Nafcillin Sodium), Nafcillin Sodium (Nafcillin Injection), Naltrexone XR Inj (Vivitrol), Naprosyn (naproxen), NeoProfen (Ibuprofen Lysine Injection), Nandrol Decanoate, Neostigmine Methylsulfate (Neostigmine Methylsulfate Injection), NEO-GAA, NeoTect (Technetium Tc 99m Depreotide Injection), Nephramine (Essential Amino Acid Injection), Neulasta (pegfilgrastim), Neupogen (Filgrastim), Novolin, Novolog, NeoRecormon, Neutrexin (Trimetrexate Glucuronate Inj), NPH (N), Nexterone (Amiodarone HCl Injection), Norditropin (Somatropin Injection), Normal Saline (Sodium Chloride Injection), Novantrone (Mitoxantrone for Injection Concentrate), Novolin 70/30 Innolet (70% NPH, Human Insulin Isophane Suspension and 30% Regular, Human Insulin Injection), NovoLog (Insulin Aspart [rDNA origin] Inj), Nplate (romiplostim), Nutropin (Somatropin (rDNA origin) for Inj), Nutropin AQ, Nutropin Depot (Somatropin (rDNA origin) for Inj), Octreotide Acetate Injection (Sandostatin LAR), Ocrelizumab, Ofatumumab Injection (Arzerra), Olanzapine Extended Release Injectable Suspension (Zyprexa Relprevv), Omnitarg, Omnitrope (Somatropin [rDNA origin] Injection), Ondansetron Hydrochloride Injection (Zofran Injection), OptiMARK (Gadoversetamide Injection), Optiray Injection (Ioversol Injection), Orencia, Osmitrol Injection in Aviva (Mannitol Injection in Aviva Plastic Vessel 250), Osmitrol Injection in Viaflex (Mannitol Injection in Viaflex Plastic Vessel 250), Osteoprotegrin, Ovidrel (Choriogonadotropin Alfa Injection), Oxacillin (Oxacillin for Injection), Oxaliplatin Injection (Eloxatin), Oxytocin Injection (Pitocin), Paliperidone Palmitate Extended-Release Injectable Suspension (Invega Sustenna), Pam idronate Disodium Injection (Pam idronate Disodium Injection), Panitumumab Injection for Intravenous Use (Vectibix), Papaverine Hydrochloride Injection (Papaverine Injection), Papaverine Injection (Papaverine Hydrochloride Injection), Parathyroid Hormone, Paricalcitol Injection Fliptop Vial (Zemplar Injection), PARP Inhibitor, Pediarix, PEGlntron, Peginterferon, Pegfilgrastim, Penicillin G Benzathine and Penicillin G Procaine, Pentetate Calcium Trisodium Inj (Ca-DTPA), Pentetate Zinc Trisodium Injection (Zn-DTPA), Pepcid Injection (Famotidine Injection), Pergonal, Pertuzumab, Phentolamine Mesylate (Phentolamine Mesylate for Injection), Physostigmine Salicylate (Physostigmine Salicylate (injection)), Physostigmine Salicylate (injection) (Physostigmine Salicylate), Piperacillin and Tazobactam Injection (Zosyn), Pitocin (Oxytocin Injection), Plasma-Lyte 148 (Multiple Electrolytes Inj), Plasma-Lyte 56 and Dextrose (Multiple Electrolytes and Dextrose Injection in Viaflex, Plastic Vessel 250), PlasmaLyte, Plerixafor Injection (Mozobil), Polidocanol Injection (Asclera), Potassium Chloride, Pralatrexate Solution for Intravenous Injection (Folotyn), Pramlintide Acetate Injection (Symlin), Premarin Injection (Conjugated Estrogens for Injection), Prep kit for Technetium Tc99 Sestamibi for Injection (Cardiolite), Prevacid I.V. (Lansoprazole for Injection), Primaxin I.V. (Imipenem and Cilastatin for Injection), Prochymal, Procrit, Progesterone, ProHance (Gadoteridol Injection Solution), Prolia (Denosumab Injection), Promethazine HCl Injection (Promethazine Hydrochloride Injection), Propranolol Hydrochloride Injection (Propranolol Hydrochloride Injection), Quinidine Gluconate Injection (Quinidine Injection), Quinidine Injection (Quinidine Gluconate Injection), R-Gene 10 (Arginine Hydrochloride Injection), Ranibizumab Injection (Lucentis), Ranitidine Hydrochloride Injection (Zantac Injection), Raptiva, Reclast (Zoledronic Acid Injection), Recombivarix HB, Regadenoson Injection (Lexiscan), Reglan Injection (Metoclopramide Injection), Remicade, Renagel, Renvela (Sevelamer Carbonate), Repronex (Menotropins for Injection), Retrovir IV (Zidovudine Injection), rhApo2L/TRAIL, Ringer's and 5% Dextrose Injection (Ringers in Dextrose), Ringer's Injection (Ringers Injection), Rituxan, Rituximab, Rocephin (ceftriaxone), Rocuronium Bromide Injection (Zemuron), Roferon-A (interferon alfa-2a), Romazicon (flumazenil), Romidepsin for Injection (Istodax), Saizen (Somatropin Injection), Sandostatin LAR (Octreotide Acetate Injection), Sclerostin Ab, Sensipar (cinacalcet), Sensorcaine (Bupivacaine HCl Injections), Septocaine (Articane HCl and Epinephrine Injection), Serostim LQ (Somatropin (rDNA origin) Injection), Simponi Injection (Golimumab Injection), Sodium Acetate (Sodium Acetate Injection), Sodium Bicarbonate (Sodium Bicarbonate 5% Injection), Sodium Lactate (Sodium Lactate Injection in AVIVA), Sodium Phenylacetate and Sodium Benzoate Injection (Ammonul), Somatropin (rDNA origin) for Inj (Nutropin), Sporanox Injection (Itraconazole Injection), Stelara Injection (Ustekinumab), Stemgen, Sufenta (Sufentanil Citrate Injection), Sufentanil Citrate Injection (Sufenta), Sumavel, Sumatriptan Injection (Alsuma), Symlin, Symlin Pen, Systemic Hedgehog Antagonist, Synvisc-One (Hylan G-F 20 Single Intra-articular Injection), Tarceva, Taxotere (Docetaxel for Injection), Technetium Tc 99m, Telavancin for Injection (Vibativ), Temsirolimus Injection (Torisel), Tenormin I.V. Injection (Atenolol Inj), Teriparatide (rDNA origin) Injection (Forteo), Testosterone Cypionate, Testosterone Enanthate, Testosterone Propionate, Tev-Tropin (Somatropin, rDNA Origin, for Injection), tgAAC94, Thallous Chloride, Theophylline, Thiotepa (Thiotepa Injection), Thymoglobulin (Anti-Thymocyte Globulin (Rabbit), Thyrogen (Thyrotropin Alfa for Injection), Ticarcillin Disodium and Clavulanate Potassium Galaxy (Timentin Injection), Tigan Injection (Trimethobenzamide Hydrochloride Injectable), Timentin Injection (Ticarcillin Disodium and Clavulanate Potassium Galaxy), TNKase, Tobramycin Injection (Tobramycin Injection), Tocilizumab Injection (Actemra), Torisel (Temsirolimus Injection), Totect (Dexrazoxane for Injection, Intravenous Infusion Only), Trastuzumab-DM1, Travasol (Amino Acids (Injection)), Treanda (Bendamustine Hydrochloride Injection), Trelstar (Triptorelin Pamoate for Injectable Suspension), Triamcinolone Acetonide, Triamcinolone Diacetate, Triamcinolone Hexacetonide Injectable Suspension (Aristospan Injection 20 mg), Triesence (Triamcinolone Acetonide Injectable Suspension), Trimethobenzamide Hydrochloride Injectable (Tigan Injection), Trimetrexate Glucuronate Inj (Neutrexin), Triptorelin Pamoate for Injectable Suspension (Trelstar), Twinject, Trivaris (Triamcinolone Acetonide Injectable Suspension), Trisenox (Arsenic Trioxide Injection), Twinrix, Typhoid Vi, Ultravist (Iopromide Injection), Urofollitropin for Injection (Metrodin), Urokinase Injection (Kinlytic), Ustekinumab (Stelara Injection), Ultralente (U), Valium (diazepam), Valproate Sodium Injection (Depacon), Valtropin (Somatropin Injection), Vancomycin Hydrochloride (Vancomycin Hydrochloride Injection), Vancomycin Hydrochloride Injection (Vancomycin Hydrochloride), Vaprisol (Conivaptan Hcl Injection), VAQTA, Vasovist (Gadofosveset Trisodium Injection for Intravenous Use), Vectibix (Panitumumab Injection for Intravenous Use), Venofer (Iron Sucrose Injection), Verteporfin Inj (Visudyne), Vibativ (Telavancin for Injection), Victoza (Liraglutide [rDNA] Injection), Vimpat (lacosamide Tablet and Injection), Vinblastine Sulfate (Vinblastine Sulfate Injection), Vincasar PFS (Vincristine Sulfate Injection), Victoza, Vincristine Sulfate (Vincristine Sulfate Injection), Visudyne (Verteporfin Inj), Vitamin B-12, Vivitrol (Naltrexone XR Inj), Voluven (Hydroxyethyl Starch in Sodium Chloride Injection), Xeloda, Xenical (orlistat), Xeomin (Incobotulinumtoxin A for Injection), Xolair, Zantac Injection (Ranitidine Hydrochloride Injection), Zemplar Injection (Paricalcitol Injection Fliptop Vial), Zemuron (Rocuronium Bromide Injection), Zenapax (daclizumab), Zevalin, Zidovudine Injection (Retrovir IV), Zithromax Injection (Azithromycin), Zn-DTPA (Pentetate Zinc Trisodium Injection), Zofran Injection (Ondansetron Hydrochloride Injection), Zingo, Zoledronic Acid for Inj (Zometa), Zoledronic Acid Injection (Reclast), Zometa (Zoledronic Acid for Inj), Zosyn (Piperacillin and Tazobactam Injection), Zyprexa Relprevv (Olanzapine Extended Release Injectable Suspension) and a combination thereof. It is to be appreciated that mutations of any or all of the drugs and biologics (e.g., antibodies, antisense, RNA interference, gene therapy, primary and embryonic stem cells, and vaccines) set forth above are considered to be within the purview of the invention.

Test Methods

It should be understood that although certain methods and equipment are described below, other methods or equipment determined suitable by one of ordinary skill in the art may be alternatively utilized.

Helium Leak

To evaluate the seal of the plunger to the barrel the leak rate of helium from the internals of an assembled syringe system to the external environment was performed. This was accomplished by placing a stopper into a dry bare glass barrel (no lubricant present) and restraining the plunger rod to prevent movement of the stopper during testing. The internal volume of the assembled syringe was evacuated through the needle by use of a vacuum and replaced with a helium atmosphere pressurized to approximately 1 psig. The space around the syringe was monitored by use of a Gas chromatography/mass spectrometry (GC/MS) tuned for helium (LACO's TitanTest™ Helium Leak Tester, Salt Lake City, UT). The area around the syringe was evacuated and analyzed for Helium concentration to determine a helium leak rate at 1 minute after helium differential pressure of approximately 15.7 psid was established.

Slide Force

Slide force was measured by filling syringe with 0.96 ml of Water For Injection (WFI) and inserting stopper using a vent tube stopper insertion machine. The syringe used was a staked needle design with a 29 gauge ½ inch needle. An appropriate plunger rod to match the stopper was fitted into the assembled syringe system without moving or disturbing the stopper. The system was placed into a holder on a force displacement analyzer and the cross head moved at a rate of 25 mm/minute until contact was made between the crosshead and the plunger rod proximal end. The test speed of 250 mm/minute was established, after which force displacement data was obtained. The maximum force obtained was recorded. The force displacement instrument used was a TA XT Plus Texture Analyzer with a TA-270N syringe test fixture (Hamilton, MA).

Contact Width

The contact width of the plunger interface with a glass barrel was measured under 30× magnification averaging 3 measurements on each rib using a Keyence digital micrometer VHX-5000 (Itasca, IL).

Barrel ID

The internal diameter of the syringe barrel was measured by use of a digital three point internal micrometer (Mitutoyo series 468, Aurora, IL).

Stopper Rib Diameter and Rib Radius

The rib diameter and rib radius of the stopper was measured using an optical measurement system (Keyence IM 6225, Itasca, IL).

EXAMPLES

A series of stoppers was fabricated as described in U.S. Pat. No. 8,722,178 to Ashmead, et al. using a halobutyl with an initial modulus of 3.5 MPa. The stoppers were sized for use with a 1 ml long bare glass (not siliconized or otherwise treated) syringe barrel with a nominal inside diameter of 6.35 mm. The stoppers differed in number, shape and size of the ribs intended to form the seal against the interior of the syringe barrel. After processing was completed, the stopper was measured using non-contact measuring equipment. The average results for each design are reported in Table 1. The stoppers were washed using warm purified water with a small amount of detergent, then rinsed and dried to remove any residual contamination from fabrication. The stoppers were inserted into bare glass barrels and tested as described herein. The results are reported in Table 2. Rib 1 is the distal end rib and subsequent ribs count up towards the proximal end.

Example 1 and Example 2 in Tables 1 and 2 are stoppers which meet the intent of this disclosure.

Comparative Example 3 in Tables 1 and 2 is an example of a stopper which has good slide force but is insufficient in diameter to achieve the required seal and is therefore insufficient.

Comparative Example 4 in Tables 1 and 2 is an example of a stopper which achieves the required seal but has excessive slide force due to a larger than desired contact between the stopper and the barrel and is therefore insufficient.

In the Tables, OD represents outer diameter and ID represents inner diameter.

TABLE 1

| Sample | OD rib 1 (mm) | Rib 1 radius (mm) | OD rib 2 (mm) | Rib 2 radius (mm) | OD rib 3 (mm) | Rib 3 radius (mm) | Rib 4 OD/rad, Rib 5 OD/rad |
|---|---|---|---|---|---|---|---|
| Example 1 | 7.42 | 0.12 | 7.41 | 0.13 | 6.73 | 0.26 | |
| Example 2 | 7.42 | 0.15 | 7.41 | 0.16 | 7.40 | 0.16 | |
| Comparative Example 3 | 6.62 | 0.90 | 6.62 | 0.89 | 6.62 | 0.89 | |
| Comparative Example 4 | 7.35 | 0.07 | 7.27 | 0.14 | 7.21 | 0.16 | 7.20/0.173, 7.23/0.21 |

TABLE 2

| Sample | Barrel ID (mm) | Compression (Rib 1) (%) | Contact width rib 1 (mm) | Total Contact width (ribs with C > 7.9%) | He leak rate (sccs) | Maximum extrusion (break loose) force (N) |
|---|---|---|---|---|---|---|
| Example 1 | 6.35 | 14.42 | 0.37 | 0.73 | $8.27^{-8}$ | 9.8 |
| Example 2 | 6.35 | 14.47 | 0.56 | 1.62 | $4.7^{-8}$ | 12.5 |
| Comparative example 3 | 6.35 | 4.06 | 0.52 | N/A | $1.5^{-5}$ | 5.2 |
| Comparative example 4 | 6.35 | 13.61 | 0.40 | 1.94 | $7.7^{-8}$ | 21.8 |

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical delivery device comprising:
a barrel having an inner surface;
a stopper contacting at least a portion of the inner surface of the barrel, the stopper comprising:
an elastomeric body,
one or more fluoropolymer layers, and
two or more ribs having a sealing surface,
wherein the one or more fluoropolymer layers is positioned on at least one of the two or more ribs, and
wherein a contact width between at least one of the two or more ribs and a portion of the inner surface of the barrel measured at a compressibility of greater than about 7.9% of the stopper is less than about 1.0 mm.

2. The medical delivery device of claim 1, wherein the inner surface is a hydrophilic inner surface.

3. The medical delivery device of claim 1, wherein the inner surface is free or substantially free of lubricants.

4. The medical delivery device of claim 1, wherein the two or more ribs are laminated with the one or more fluoropolymer layers.

5. The medical delivery device of claim 1, wherein the stopper further comprises a sliding surface that is less than about 2.0 mm.

6. The medical delivery device of claim 1, wherein the inner surface is bare glass.

7. The medical delivery device of claim 1, wherein each rib of the two or more ribs having a sealing surface comprises a radius of curvature at an apex of each respective rib that is less than about 0.22 mm.

8. The medical delivery device of claim 7, wherein a ratio of a maximum outer diameter of all the ribs having a sealing surface to an inner diameter of the inner surface of the barrel is greater than about 1.08.

9. The medical delivery device of claim 8, wherein a maximum outer diameter of the ribs having a sealing surface is greater than about 5.0 mm, an inner diameter of the inner surface of the barrel is between about 4.65 mm and about 11.85 mm, and a ratio of the maximum outer diameter of the ribs having a sealing surface to an inner diameter of the inner surface of the barrel is greater than about 1.08.

10. The medical delivery device of claim 1, wherein the one or more fluoropolymer layers comprise a single layer of densified expanded polytetrafluoroethylene.

11. The medical delivery device of claim 1, wherein each rib of the two or more ribs comprises a radius of curvature at an apex of each respective rib of less than about 0.22 mm.

12. The medical delivery device of claim 11, wherein a ratio of a maximum outer diameter of all the ribs having a sealing surface to an inner diameter of the inner surface of the barrel is greater than about 1.08.

13. The medical delivery device of claim 11, wherein a maximum outer diameter of the ribs having a sealing surface is greater than about 5.0 mm, an inner diameter of the inner surface of the barrel is between about 4.65 mm and about 11.85 mm, and a ratio of the maximum outer diameter of the ribs having a sealing surface to an inner diameter of the inner surface of the barrel is greater than about 1.08.

14. The medical delivery device of claim 1, wherein the one or more fluoropolymer layers comprise a composite fluoropolymer film having a barrier layer and a porous layer, the barrier layer comprising at least one member selected from densified expanded polytetrafluoroethylene, polytetrafluoroethylene, fluorinated ethylene propylene, polyethylene, polypropylene, polyvinylidene fluoride, polyvinyl fluoride, perfluoropropyl vinyl ether, or a perfluoroalkoxy polymer and copolymers and combinations thereof.

15. The medical delivery device of claim 1, wherein each rib of the two or more ribs comprises a radius of curvature at an apex of curvature of each respective rib that is less than about 0.22 mm.

16. The medical delivery device of claim 15, wherein a ratio of a maximum outer diameter of all the ribs having a sealing surface to an inner diameter of the inner surface of the barrel is greater than about 1.08.

17. The medical delivery device of claim 15, wherein a maximum outer diameter of the ribs having a sealing surface is greater than about 5.0 mm, an inner diameter of the inner surface of the barrel is between about 4.65 mm and about 11.85 mm, and a ratio of the maximum outer diameter of the ribs having a sealing surface to an inner diameter of the inner surface of the barrel is greater than about 1.08.

\* \* \* \* \*